US 6,699,668 B1

(12) United States Patent
Schmidt et al.

(10) Patent No.: US 6,699,668 B1
(45) Date of Patent: Mar. 2, 2004

(54) MASS LABEL LINKED HYBRIDISATION PROBES

(75) Inventors: Günter Schmidt, Houghton (GB); Andrew Hugin Thompson, Alloway (GB); Robert Alexander Walker Johnstone, Bedington (GB)

(73) Assignee: XZillion GmbH & Co. (DE)

( * ) Notice: Subject to any disclaimer, the term of this patent is extended or adjusted under 35 U.S.C. 154(b) by 0 days.

(21) Appl. No.: 09/987,679

(22) Filed: Nov. 15, 2001

Related U.S. Application Data

(62) Division of application No. 09/341,646, filed on Sep. 20, 1999, now abandoned.

(30) Foreign Application Priority Data

| Jan. 15, 1997 | (GB) | 9700746 |
| Aug. 28, 1997 | (GB) | 9718255 |
| Dec. 19, 1997 | (GB) | 9726953 |

(51) Int. Cl.[7] ............ C12Q 1/68; C12P 19/34; C07H 21/04
(52) U.S. Cl. .......... 435/6; 435/91.1; 436/173; 536/23.1
(58) Field of Search ............... 435/6; 536/243, 536/23.1; 436/518, 536

(56) References Cited

U.S. PATENT DOCUMENTS 5,760,201 A * 6/1998 Glazer et al. ............ 435/6
6,027,890 A * 2/2000 Ness et al. ............... 435/6
6,051,378 A * 4/2000 Monforte et al. ......... 435/6

FOREIGN PATENT DOCUMENTS

| CA | 2168010 A1 | 2/1995 |
| EP | 0 735 144 A1 * | 10/1996 |
| EP | 0 735 144 | 10/1996 |
| WO | WO 94/16101 | 7/1994 |
| WO | WO 95/04160 * | 2/1995 |
| WO | WO 96/32504 | 10/1996 |
| WO | WO 97/27325 | 7/1997 |
| WO | WO 98/10095 | 3/1998 |
| WO | WO 98/26095 A1 | 6/1998 |

OTHER PUBLICATIONS

Dong–Jing Fu et al., Sciences of USA, vol. 92, No. 22, Oct. 24, 1995, pp. 10162–10166, XP000602286.

Fu D–J et al., Genetic Analysis: Biomolecular Engineering, vol. 12, No. 3/04, Jan. 1996, pp. 137–142, XP000602230.

* cited by examiner

Primary Examiner—Kenneth R. Horlick
Assistant Examiner—Cynthia Wilder
(74) Attorney, Agent, or Firm—Burns Doane Swecker & Mathis, LLP

(57) ABSTRACT

An array of hybridisation probes, each of which comprises a mass label linked to a known base sequence of predetermined length, wherein each mass label of the array, optionally together with the known base sequence, is relatable to that base sequence by mass spectrometry.

25 Claims, 30 Drawing Sheets

(1)

(2)

(3)

(4)

(1)

(2)

(3)

(4)

FT 9

FT 17

FT 18/1

FT23

MASS LABEL LINKED HYBRIDISATION PROBES

This application is a divisional of U.S. application Ser. No. 09/341,646, filed on Sep. 20, 1999 abandoned, which was a national stage filing under 35 U.S.C. §371 of International Application No. PCT/GB98/00127 filed on Jan. 15, 1998, which International Application was published by the International Bureau in English on Jul. 23, 1998.

FIELD OF THE INVENTION

The present invention relates to an array of hybridisation probes, use of hybridisation probes, a method of determining hybridisation of an array of such probes and methods for characterising cDNA and sequencing nucleic acid.

BACKGROUND TO THE INVENTION

Mass spectrometry is a highly sensitive technique for determining molecular masses, so sensitive that it can be used to give detailed structural information as well. Essentially, the molecule(s) to be analysed is vaporised and ionised into a vacuum. The vapor phase ions are accelerated through electromagnetic fields and their mass/charge ratio is determined by analysis of the molecules behaviour in the electromagnetic fields. Various mass spectrometry technologies exist determined by the main targets of the systems or on the various ionisation techniques that they employ. On the whole mass spectrometry is used for direct analysis of molecules in order to determine their mass; identify them or acquire structural information. (For a textbook on mass spectrometry see reference 1)

Combinatorial chemistry (for a review of this field see reference 2) has lead to more specific requires for indirect analysis of molecules. Various strategies now exist to generate large numbers of related molecules, using solid phase synthesis techniques, in a combinatorial manner. Since most systems generate individual molecules on beads, these can be screened for desirable properties. However, it is often the case that molecule being screened is not directly recoverable or difficult to analyse directly for other reasons so indirect labelling of beads and hence their molecules has been proposed as a solution. Most techniques for 'encoding' (see reference 3) combinatorial libraries seem to involve using labels that are in some sense capable of being 'sequenced' (see reference 4), for example amino acids and nucleic acids are often used to encode libraries because the technologies to sequence these are routine and relatively rapid for short peptides and oligonucleotides, an analysis that is often also performed by mass spectrometry these days. Other organic entities are sequencable such as halogenated benzenes and secondary amides and can be used for these purposes (see references 5 and 6).

An alternative approach (see reference 7) uses a variety of combinatorial monomers that can be enriched in particular isotopes to generate labels that give unique isotope signatures in a mass spectrum. This approach allows the generation of large numbers of labels that have distinct patterns of isotope peaks in restricted regions of the mass spectrum. This method is ideal for uniquely identifying a single compound whose bead has been isolated from a large combinatorial library, for example but would almost certainly have problems resolving large numbers of molecules simultaneously.

References 15 to 17 disclose applications of mass spectrometry to detect binding of various ligands.

SUMMARY OF THE INVENTION

The present invention provides an array of hybridisation probes, each of which comprises a mass label linked to a known base sequence of predetermined length, wherein each mass label of the array, optionally together with the known base sequence, is relatable to that base sequence by mass spectrometry. Preferably, each of the hybridisation probes comprises a mass label cleavably linked to a known base sequence of predetermined length, wherein each mass label of the array, when released from its respective base sequence, is relatable to that base sequence by mass spectrometry, typically by its mass/charge ratio which is preferably uniquely identifiable in relation to every other mass label in the array.

The present invention further provides use of a hybridisation probe, comprising a mass label linked to a known base sequence of predetermined length, in a method for determining hybridisation of the probe by mass spectrometry of the mass label optionally together with the known base sequence. Preferably, the hybridisation probe comprises a mass label cleavably linked to a known base sequence of predetermined length.

The present invention further provides a method for determining hybridisation of a probe with a target nucleic acid, which method comprises
(a) contacting target nucleic acid with a hybridisation probe, which comprises a mass label linked to a known base sequence of predetermined length, under conditions to hybridise the probe to the target nucleic acid and optionally removing unhybridised material; and
(b) identifying the probe by mass spectrometry.

The present invention further provides a method for determining hybridisation of an array of probes with a target nucleic acid, which method comprises
(a) contacting target nucleic acid with each hybridisation probe of the array under conditions to hybridise the probe to the target nucleic acid, and optionally removing unhybridised material, wherein each probe comprises a mass label linked to a known base sequence of predetermined length; and
(b) identifying the probe by mass spectrometry.

Preferably, the or each mass label is cleavably linked to its respective known base sequence and each hybridised probe is cleaved to release the mass label, which released label is identified by mass spectrometry.

The predetermined length of the base sequence is usually from 2 to 25.

Each mass label may be cleavably linked to the known base sequence by a link which may be a photocleavable link, a chemically cleavable link or a thermally cleavable link. According to one embodiment, the link cleaves when in a mass spectrometer, for example in the ionisation chamber of the mass spectrometer. This has the advantage that no cleavage of the link need take place outside of the mass spectrometer. By appropriate selection of the link, cleavage is effected in the mass spectrometer so as to afford a rapid separation of the known base sequence from the mass label so that the mass label can be readily identified. The link is preferably less stable to electron ionisation than the mass label. This allows cleavage of the link without fragmentation of any part of the mass label inside the mass spectrometer.

In a preferred embodiment, the mass label is stable to electron ionisation at 50 volts, preferably at 100 volts. Conditions of electron ionisation occurring in mass spectrometers can cause fragmentation of molecules and so it is convenient to measure stability of a mass label in terms of its ability to withstand electron ionisation at a particular voltage. Stability to electron ionisation is also a useful guide as to stability of the molecule under collision induced dissociation conditions experienced in a mass spectrometer.

Preferably, the mass labels are resolvable in mass spectrometry from the known base sequences. This is advantageous because the need to separate or purify each mass label from their respective base sequences is avoided. Accordingly, in a preferred embodiment, the mass label and the known base sequences are not separated before entry into the mass spectrometer.

In a further preferred embodiment, the method is exclusively in line. By in-line is meant that at no stage in the method is there a step which is performed off-line. This is advantageous because the method can be performed as a continuous method and may be readily automatable.

In one embodiment, each mass label is designed to be negatively charged under ionisation conditions. This has the advantage that buffer conditions can be arranged whereby nucleic acid accompanying the mass label is positively charged. When in a mass spectrometer, this enables ready separation of the mass label from the DNA and results in less background noise in the mass spectrum.

Preferably the known base sequence has linked thereto a plurality of identical mass labels. Using a plurality of identical mass labels has the advantage that simultaneous cleavage or the plurality of mass labels gives rise to a higher signal because a higher concentration of mass labels may be measured.

In one embodiment, the known base sequence comprises a sticky end of an adaptor oligonucleotide containing a recognition site for a restriction endonuclease which cuts at a predetermined displacement from the recognition site.

This invention advocates the use of labels with well-behaved mass spectrometry properties, to allow relatively large numbers of molecules to be identified in a single mass spectrum. Well behaved meaning that the molecules minimise the number of peaks that they generate in a spectrum by preventing multiple ionisation states and not using especially labile groups. Several decades of mass spectrometry in organic chemistry has identified certain molecular features that are favorable for such use and certain features to be avoided.

Mass Spectrometry for Analysis of Labelled Molecules

It is possible to label molecules particularly biological molecules with mass, as an indicator of the molecules identity. A code relating a molecule's mass to its identity is easy to generate, e.g. given a set of molecules which it is desirable to identify one can simply select an increasing mass for each distinct molecule to be identified. Obviously many molecules can be identified on the basis of their mass alone and labelling may seem superfluous. It may be the case that certain sets of molecules, although unique, may have closely related masses and be multiply ionisable, making resolution in the mass spectrometer difficult hence the utility of mass-labelling. This is particularly true of nucleic acids which are often isobaric but still distinct, e.g. the sequence TATA is distinct from TTAA, TAAT, etc. but in a mass spectrometer these would be difficult to resolve. Furthermore one might like the molecules to be identified to perform a certain function as well as being detectable and this means direct detection might be impossible so a removable label that can be independently detected is of great utility. This will allow large numbers of molecules that may be very similar to be analysed simultaneously for large scale screening purposes.

This invention describes the use of libraries of mass labels which identify the sequence of a covalently linked nucleic acid probe. The construction of mass labels is relatively simple for a qualified organic chemist. This makes it easy to produce labels that are controllably removable from their respective probe and which have beneficial physical properties that aid ionisation into a mass spectrometer and that aid detection and resolution of multiple labels over a large range of relative quantities of those labels.

The present invention will now be described in further detail by way of example only, with reference to the accompany no drawings, in which.

APPLICATIONS OF MASS LABELLING TECHNOLOGY

Figure 1A:
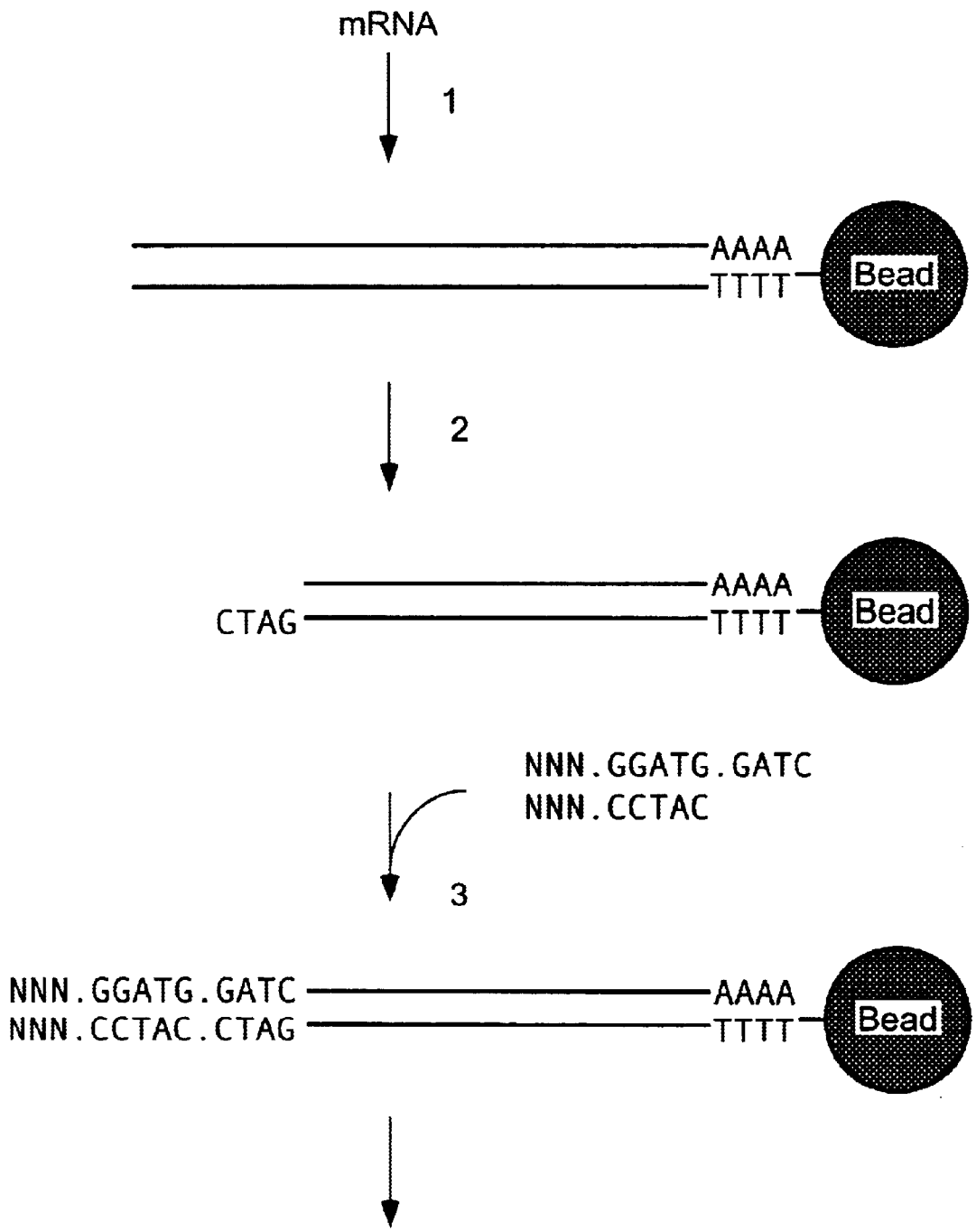
FIGS. 1a and 1b show use of mass labelled hybridisation probes according to the present invention in a method of gene expression profiling.
Figure 1B:
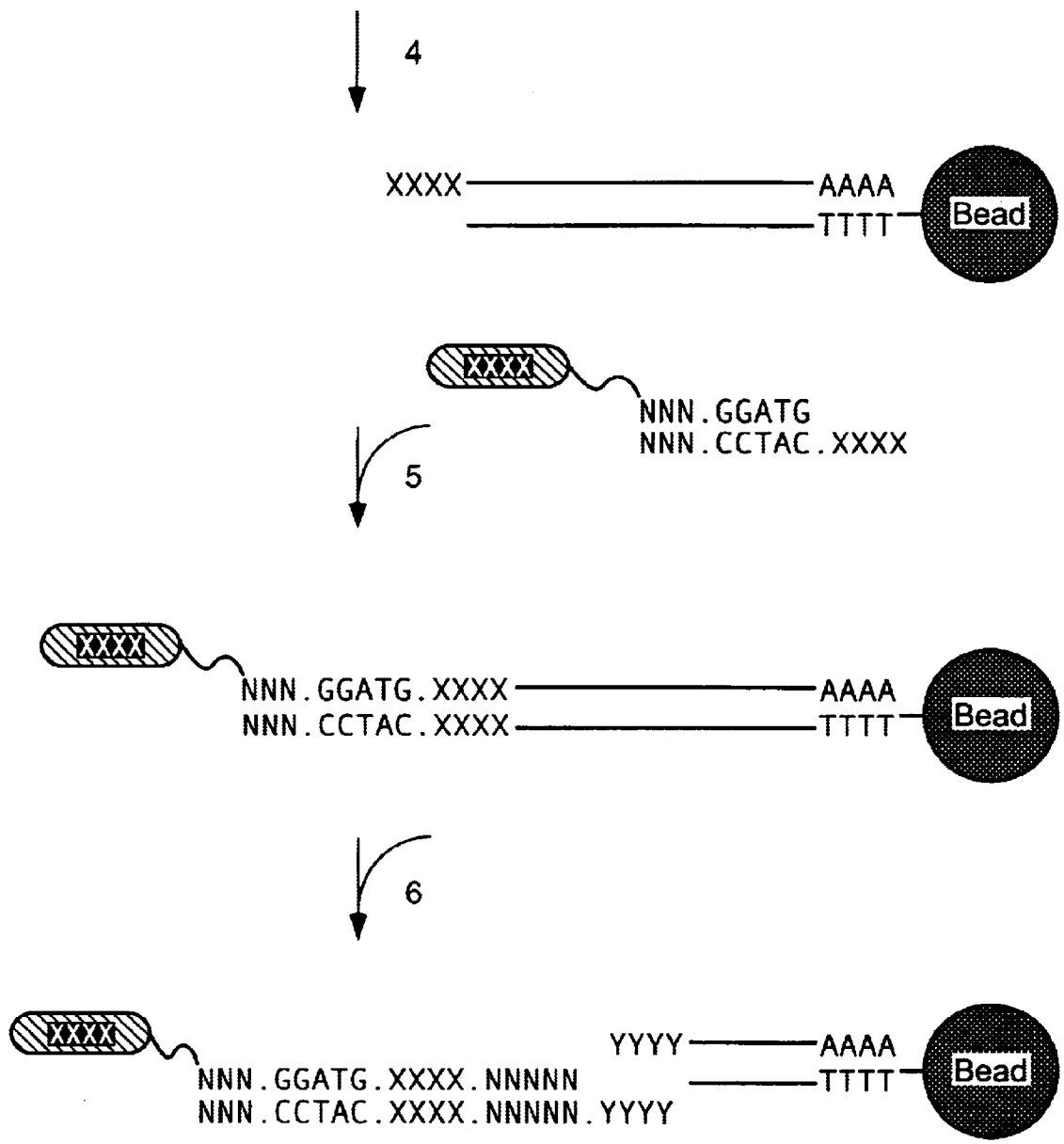
Figure 1C:
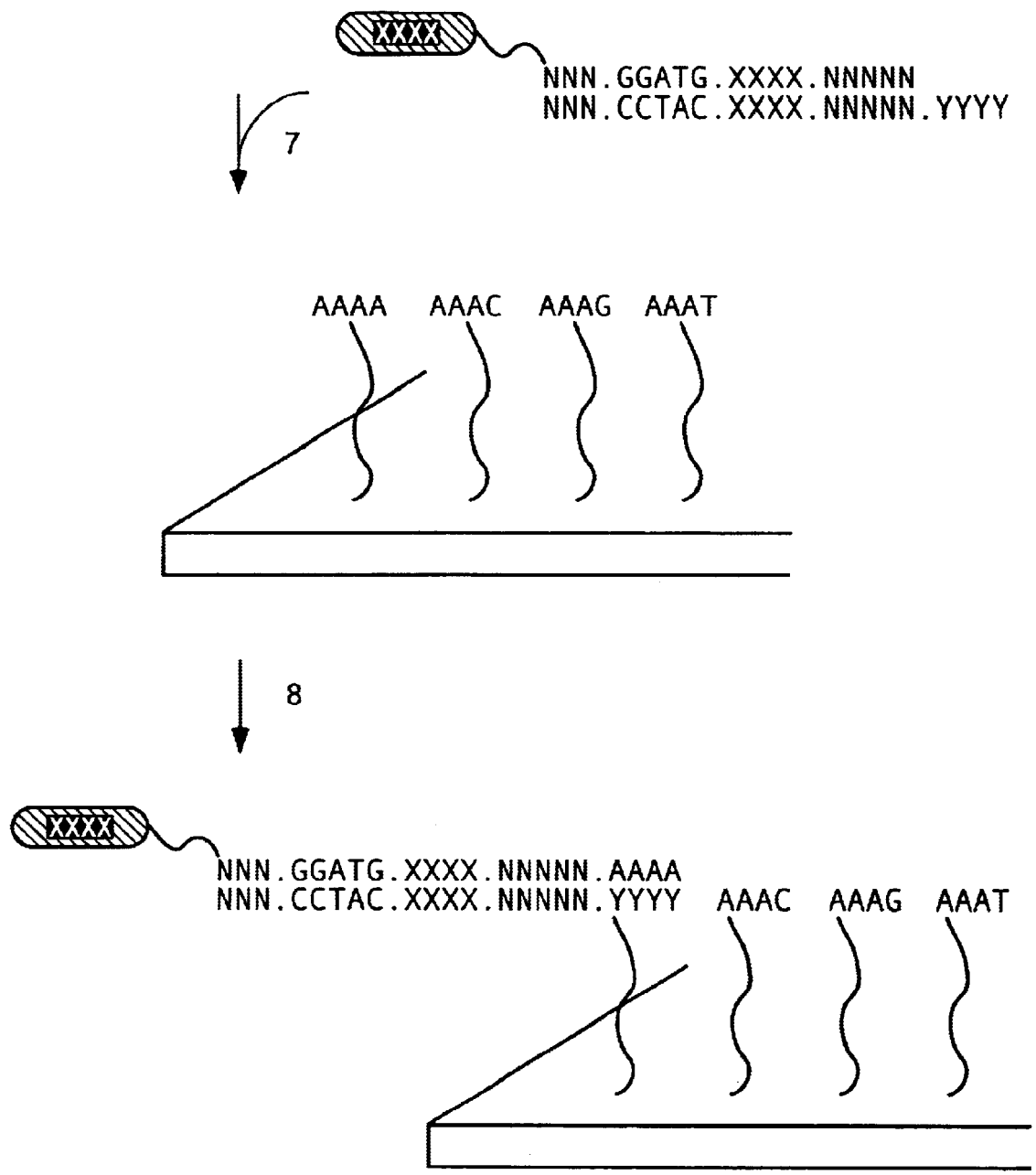
Figure 1D:
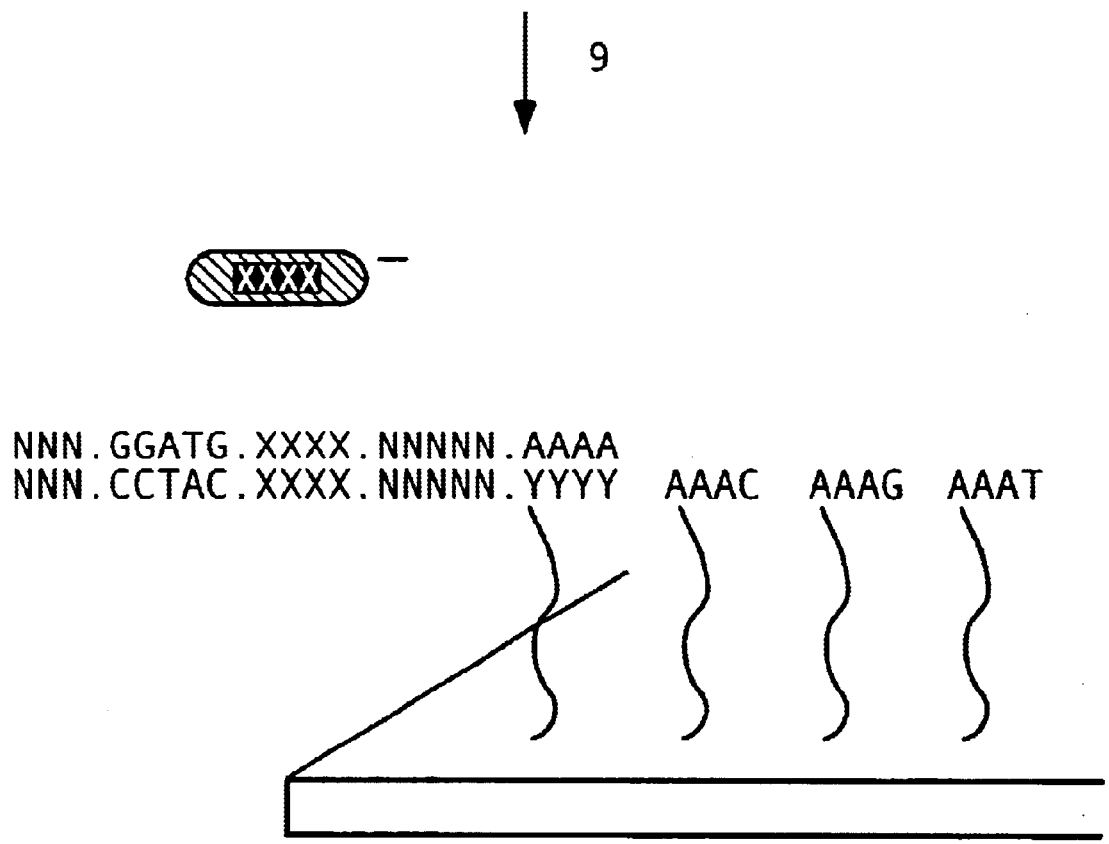

There are two key mass spectrometry ionisation technologies that are routinely used in biological analysis. These are electrospray mass spectrometry (ESMS) and MALDI TOF mass spectrometry. ESMS is essentially a technique that allows ionisation from the liquid phase to the vapour phase while MALDI techniques essentially allow ionisation from solid phase to vapour phase. Much molecular biology is carried out in the liquid phase or uses solid phase chemistry in a liquid medium through which reagents can be added and removed from molecules immobilised on solid phase supports. In a sense these two techniques are complementary allowing analysis of both solid phase and liquid phase elements.

Use of Mass-labelled Adaptor Molecules for Gene Profiling

The Gene Profiling technology described in reference 8 provides a method for the analysis of patterns of gene expression in a cell by sampling each cDNA within the population of that cell. According to this patent application, a method is provided for characterising cDNA. The method comprises:

(a) cutting a sample comprising a population of one or more cDNAs or isolated fragments thereof each bearing one end of the cDNA such as the poly-A tail with a first sampling endonuclease at a first sampling site of known displacement from a reference site proximal to the end of the cDNA to generate from each cDNA or isolated fragment thereof a first and second sub-fragment, each comprising a sticky end sequence of predetermined length and unknown sequence, the first sub-fragment having the end of the cDNA;

(b) sorting either the first or second sub-fragments into sub-populations according to their sticky end sequence and recording the sticky end sequence of each sub-population as the first sticky end;

(c) cutting the sub-fragments in each sub-population with a second sampling endonuclease, which is the same as or different from the first sampling endonuclease, at a second sampling site of known displacement from the first sampling site to generate from each sub-fragment a further sub-fragment comprising a second sticky end sequence of predetermined length and unknown sequence; and (d) determining each second sticky end sequence;

wherein the aggregate length of the first and second sticky end sequences of each sub-fragment is from 6 to 10; and wherein the sequences and relative positions of the reference site and first and second sticky ends characterise the or each cDNA.

The sample cut with the first sampling endonuclease preferably comprises isolated fragments of the cDNAs produced by cutting a sample comprising a population of one or more cDNAs with a restriction endonuclease and isolating fragments whose restriction site is at the reference site.

The first sampling endonuclease preferably binds to a first recognition site and cuts at the first sampling site at a predetermined displacement from the restriction site of the restriction endonuclease. In accordance with this aspect of the present invention, the first recognition site is provided in a first mass labelled adaptor oligonucleotide as described above, which is hybridised to the restriction site of the isolated fragments. According to this method, the aggregate length of the first and second sticky end sequences of each sub-fragment is preferably 8.

In one embodiment, the sampling system takes two samples of 4 bp from each cDNA in a population and determines their sequence with respect to a defined reference point. To effect this each cDNA in a population is immobilised and may be cleaved with a restriction endonuclease. An adaptor is ligated to the resulting known sticky-end. The adaptor is designed to carry the binding site for a type IIs restriction endonuclease. An ambiguous 4 bp sticky-end is exposed at the adaptored terminals of each cDNA in the population using the type IIs restriction endonuclease. A family of adaptor molecules is used to probe those 4 exposed bases. With fluorescence based systems only four probe molecules, out of a possible 256 can be added at a time to probe a pool of cDNAs, as discussed in reference 8. This is clearly going to be a slow method for determining the sequence of the 4 base pairs. With mass labelled adaptors, all 256 possible 4 bp adaptors can be added to a pool of exposed cDNAs at the same time, greatly speeding up the gene profiling invention. This is essential for a commercially viable technology.

Such a system could be made compatible with ESMS. In the gene profiling invention the cDNA population is sorted into 256 subsets on the basis of sequence exposed by a type IIs restriction endonuclease. This sorting produces 256 populations of cDNA in 256 wells. A second 4 bp of sequence can be exposed for each cDNA by a second cleavage with a type IIs restriction endonuclease and these 4 bases can then be determined by ligation of mass-labelled adaptors Mass Spectrometry Based Oligonucleotide Chip Readers (MALDI)

Oligonucleotide Arrays

Various nucleic acid assays can be performed using arrays of oligonucleotide synthesised on a planar solid phase substrate like a glass slide. Such arrays are generally constructed such that the slide is divided into distinct zones or fields and each field bears only a single oligonucleotide. Hybridisation of a labelled nucleic acid to the array is determined by measuring the signal from the labelled nucleic acid from each field of the array. Determination of mRNA levels can be effected in a number of ways. One can readily convert poly-A bearing mRNA to cDNA using reverse transcription. Reverse Transcriptase PCR (RTPCR) methods allow the quantity of single RNAs to be determined, but with a relatively low level of accuracy. Arrays of oligonucleocides are a relatively novel approach to nucleic acid analysis, allowing mutation analysis, sequencing by hybridisation and mRNA expression analysis. Methods of construction of such arrays have been developed, (see for example: references 9, 10, 11) and further methods are envisaged.

Hybridisation of labelled nucleic acids to oligonucleotide arrays of the sort described above is typically detected using fluorescent labels. Arrays of oligonucleotides or cDNAs can be probed with nucleic acids labelled with fluorescent markers. For an oligonucleotide chip this would reveal to which oligonucleotides a labelled nucleic is complementary by the appearance of fluorescence in the fields of the array containing oligonucleotides to which the labelled nucleic acid hybridises. Such oligonucleotide arrays could be read using MALDI mass spectrometry if nucleic acids that are hybridised to the oligonucleotide array were labelled with mass labels. The mass labels would preferably be linked to their corresponding nucleic acid using a photo-cleavable linker. These mass labels could incorporate laser excitable agents into their structure or the oligonucleotide array could be treated with appropriate desorption agents after a hybridisation reaction has been performed, such as 3-hydroxypicolinic acid. Once a mass labelled nucleic acid (s) has hybridised to the chip, the linker between mass label and nucleic acid can be cleaved by application of laser light of the appropriate frequency. The labels can then be desorbed from specific regions of an oligonucleotide array by scanning those regions with laser light of the appropriate frequency. The identity of the hybridised nucleic acid at a particular field of the oligonucleotide array can then be determined from the mass of the label that is desorbed from that field of the array.

The advantage of this over using fluorescence based systems is simply in the number of labels that are available. Fluorescent dye based techniques are severely limited by problems of spectral overlap, which limits the number of dyes hat can be generated for simultaneous use with fluorescence based readers. A very much larger number of mass labels can be generated using mass spectrometry as the label detection system.

Oligonucleotide arrays can be directly adapted for use with the gene-profiling technology disclosed in reference 12. An array that bears all 256 possible 4 base oligonucleotides at defined points on its surface can be used to effect the sorting step required by that invention, discussed above. In order that this chip-based embodiment of the profiling system be compatible with mass-spectrometric analysis one requires that the labels used on the adaptors for determining the second 4 base sample of sequence be MALDI compatible so that the oligonucleotide chip can be scanned by an Ultra-Violet laser in a MALDI spectrometer. This will allow an eight base signature to be determined for each cDNA in a population with a single sample of DNA taken from a single immobilised source and analysed in one series of laser scans. The region of the chip from which a set of labels is desorbed from identifies the first 4 bp of the signature while the composition of the labels identifies the second 4 bases of the signature and the relative quantities of each cDNA.

Gene Profiling using Liquid Chromatography Mass Spectrometry:

The gene profiling process operates in a two stage process, molecular sorting of signatures followed by analysis of probe molecules ligated to the sorted signatures. The MALDI approach uses an oligonucleotide array to effect sorting of the signatures. An alternative to the use of an array is affinity chromatography. An affinity column for the sorting of signatures on the basis of an ambiguous sticky-end of a predetermined length. To sort signatures with an ambiguous sticky-end of 4 bp, one can derivitise beads appropriate for use in an HPLC format with the 256 possible 4-mers at the sticky-end. Such a column may be loaded with the signatures dissolved in a buffer favouring hybridisation to the 4 mers on the derivitised beads. This will drive the hybridisation equilibrium in favour of hybridisation. The column may then be washed with gradually increasing concentrations of a buffer that inhibits hybridisation. Signatures terminating with AAAA or TTTT sticky ends will be released first while GGGG and CCCC signatures will be released last. To ensure separation of signatures that are the complement of each other one can derivitise beads with base analogs so that the hybridisation affinity of a guanine in a signature to a cytosine on a bead is different to the hybridisation of a cytosine in a signature sticky-end to a guanosine on a bead. Furthermore, one can ensure that each 4-mer is present in a different relative concentration on the beads to any other.

Such an affinity column should allow a population of signatures to be sorted into 256 fractions according to the sequence of its ambiguous sticky-end. Such fractions can then be loaded directly into an Electrospray Mass Spectrometer for analysis.

Use of mass labelled adaptor molecules for Sequencing DNA:

A sequencing technology is described in reference 13, in which a method for sequencing nucleic acid is provided, which comprises:

(a) obtaining a target nucleic acid population comprising nucleic acid fragments in which each fragment is present in a unique amount and bears at one end a sticky end sequence of predetermined length and unknown sequence, (b) protecting the other end of each fragment, and (c) sequencing each of the fragments by (i) contacting the fragments with an array of adaptor oligonucleotides in a cycle, each adaptor oligonucleotide bearing a label, a sequencing enzyme recognition site, and a known unique base sequence of same predetermined length as the sticky end sequence, the array containing all possible base sequences of that predetermined length; wherein the cycle comprises sequentially contacting each adaptor oligonucleotide of the array with the fragments under hybridisation conditions in the presence of a ligase, removing any ligated adaptor oligonucleotide and recording the quantity of any ligated adaptor oligonucleotide by detection of the label, then repeating the cycle, until all of the adaptors in the array have been tested;

(ii) contacting the ligated adaptor oligonucleotides with a sequencing enzyme which binds to the recognition site and cuts the fragment to expose a new sticky end sequence which is contiguous with or overlaps the previous sticky end sequence;

(iii) repeating steps (i) and (ii) for a sufficient number of times and determining the sequence of the fragment by comparing the quantities recorded for each sticky end sequence. Preferably the predetermined length of the base sequence of the sticky ends is from 3 to 5. According to the present invention each adaptor oligonucleotide bears a mass label, as described above. This is similar in principal to the Gene Profiling system described in reference 8, in that DNA molecules are immobilised and have 4 base sequences exposed at their termini by type IIs restriction endonucleases in an iterative cycle. These are also probed with adaptor molecules so for the same reasons as the Gene Profiling use of mass-labelled adaptors is advantageous although labels compatible with a liquid phase system would be more appropriate, such as for use with an electrospray mass spectrometry system since the sequencing invention is an iterative process and sequence samples are analysed continuously rather than just once as in the Gene Profiling system.

Hybridisation Assays

Reference 14 discloses a method to identify sites in the tertiary structure of the RNA that are accessible to oligonucleotides that does not require amplification of oligonucleotides or any form of electrophoresis. The binding of short oligonucleotide probes; preferably 4-mers, to an mRNA is detected and the pattern of binding is co-related to the primary structure of the mRNA. An accessible region will have a number of probes binding to it with a high affinity and the sequences of those probes should be complementary to the primary sequence at that accessible region. The sequences of the probes should also overlap. In the above patent application, the mRNA or the probes are immobilised onto a solid phase substrate and labelled probes or mRNA, respectively, are hybridised to the captured nucleic acids. The preferred method of labelling disclosed in reference 14 is fluorescent labelling, but it is clear that mass-labelled nucleic acids could be used instead.

Numerous hybridisation based assays are known in the art, although of particular importance is Southern blotting and other methods of detecting the presence of a specific sequence in a sample. It should be clear to those skilled in the art that mass labelled hybridisation probes can be used for these purposes. It should also be clear that the advantage of using mass labelled hybridisation probes is the ability to probe for multiple sequences simultaneously with a multiple, uniquely mass labelled nucleic acid hybridisation probes.

Reference 15 discusses a variety of hybridisation assays compatible with mass-labelled nucleic acid probes.

Analysis of Mass-Labelled Nucleic Acids by Mass Spectrometry: The essential features of a mass spectrometer are as follows: Inlet System→Ion Source→Mass Analyser→Ion Detector→Data Capture System. For the purposes of analysing biomolecules, which for this application are mass-labelled nucleic acid probes, the critical feature is the the inlet system and ion source. Other features of importance for the purposes of biological analysis are the sensitivity of the mass analyser/detector arrangements and their ability to quantify analyte molecules.

Ionisation Techniques

For many biological mass spectrometry applications, so called 'soft' ionisation techniques are used. These allow large molecules such as proteins and nucleic acids to be ionised essentially without fragmentation. The liquid phase techniques allow large biomolecules to enter the mass spectrometer in solutions with mild pH and at low concentrations. A number of techniques are ideal for use with this invention, including but not limited to Electrospray Ionisation, Fast Atom Bombardment and Matrix Assisted Laser Desorption Ionisation (MALDI).

Electrospray Ionisation

Electrospray ionisation requires that a dilute solution of a biomolecule be nebulised into the spectrometer, i.e., injected as a fine spray. For example, solution may be sprayed from the tip of a capillary tube by a stream of dry nitrogen and under the influence of an electrostatic field. The mechanism of ionisation is not fully understood but is thought to be broadly as follows. In a stream of nitrogen the solvent evaporates. As the droplets become smaller, the concentration of the biomolecule increases. Under the spraying conditions, most biomolecules carry a net positive or negative charge, which increases electrostatic repulsion between the dissolved biomolecules. As evaporation of solvent continues this repulsion eventually becomes greater than the surface tension of the droplet and the droplet 'explodes' into smaller droplets. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance for the use of mass labels in that it imparts very little extra internal energy into ions so that the internal energy distribution within a population tends to fall into a narrow range. The ions are accelerated out of the ionisation chamber under the influence of the applied electric field gradient. The direction of this gradient determines whether positive or negative ions pass into the mass analyser. The strength of the electric field adds to their kinetic energies. This in turn leads to more or less energy transfer during collisions of ions and neutral molecules, which may then give rise to fragmentation. This is of significance when considering fragmentation of ions in the mass spectrometer. The more energy imparted to a population of ions the more likely it is that fragmentation will occur through collision of analyte molecules with the bath gas or solvent vapour present in the source. By adjusting the voltage used to accelerate ions in the ionisation chamber one can control the fragmentation of ions. This phenomenon is advantageous when fragmentation of ions is to be used as a means of cleaving a label from a mass labelled nucleic acid.

Matrix Assisted Laser Desorption Ionisation (MALDI)

MALDI requires that the biomolecule be embedded in a large molar excess of a photo-active 'matrix'. The application of laser light of the appropriate frequency (266 nm for nicotinic acid) results in the excitation of the matrix which in turn leads to excitation and ionisation of the embedded biomolecule. This technique imparts a significant quantity of translational energy to ions but tends not to induce excessive fragmentation. Electric fields can again be used to control fragmentation with this technique. MALDI techniques can be used in two ways. Mass-labelled DNA may be embedded in a matrix, so that the labels themselves are not specifically excitable by the laser or labels could be constructed so as to contain the necessary groups that would allow laser excitation. The latter approach would mean the label would not need to be embedded in a matrix before performing mass spectrometry. Such groups include nicotinic, sinapinic or cinnamic acid moieties. MALDI-based cleavage of labels would probably be most effective with a photocleavable linker as this would avoid a cleavage step prior to performing MALDI mass spectrometry. The various excitable ionisation agents have different excitation frequencies so that a different frequency can be chosen to trigger ionisation from that used to cleave the photolysable linker. These excitable moieties could derivitised using standard synthetic techniques in organic chemistry to give a variety of labels having a range of masses. The range could be constructed in a combinatorial manner.

Fast Atom Bombardment

Fast Atom Bombardment has come to describe a number of techniques for vaporising and ionising relatively involatile molecules. The essential principal of these techniques is that samples are desorbed from surfaces by collision of the sample with accelerated atoms or ions, usually xenon atoms or caesium ions. The samples may be coated onto a solid surface as for MALDI but without the requirement of complex matrices. These techniques are also compatible with liquid phase inlet systems—the liquid eluting from a capillary electrophoresis inlet or a high pressure liquid chromatograph passes through a frit, essentially coating the surface of the frit with analyte solution which can be ionised from the frit surface by atom bombardment.

Quantification and Mass Spectrometry

For the most part, many biochemical and molecular biological assays are quantitative. A mass spectrometer is not a simple device for quantification but use of appropriate instrumentation can lead to great sensitivity. The number of ions reaching a mass spectrometer detector is not a direct measure of the number of molecules actually in the ion source. The relationship between numbers of ions and the initial concentration of biomolecules is a complex function of ionisation behaviour. Quantification may be effected by scanning the mass spectrum and counting ions at each mass/charge ratio scanned. The count is integrated to give the total count at each point in the spectrum over a given time. These counts can be related back to the original qunatities of source molecules in a sample. Methods for relating the ion count or current back to the quantity of source molecule vary. External standards are one approach in which the behaviour of the sample molecules is determined prior to measurement of unknown sample. A calibration curve for each sample molecule can be determined by measuring the ion current for serial dilutions of a sample molecule when fed into the instrument configuration being used.

Internal standards are probably the more favoured approach rather than external standards, since an internal standard is subjected to the same experimental conditions as the sample so that any experimental vagaries will affect both the internal control and the sample molecules. To determine the amount substrate in a sample, a known amount of an internal standard is added to the sample. The internal standard is chosen so as to have a similar ionisation behaviour as that of the substrate being measured. The ratio of sample ion count to internal standard ion count can be used to determine the quantity of sample. Choosing appropriate standards is the main difficult with this approach. The internal standard should be similar to that of the substrate but not have the same mass. The most favourable approach is to use isotopically-labelled internal standards. This approach might be less desirable than the use external standards if large numbers of mass-labels are needed because of the expense of synthesising appropriate internal standards. However, such labels would give better qunatification than would external standards. An alternative to isotope labelling is to find an internal standard that has similar but not identical chemical behaviour to that of the sample in the mass spectrometer. Finding such analogues is difficult and could be a significant task for large families of mass labels.

A compromise approach might be appropriate because the large families of mass labels to be synthesised combinatorially, will be related chemically. A small number of internal controls might be used, where each individual control determines the quantities of a number of mass labels. The precise relationship between internal standard and each mass label might be determined in external calibration experiments to compensate for any differences between their ionisation charateristics.

The configuration of the mass spectrometer is critical to determining the actual ion count. The ionisation and mass separation methods are particularly sensitive in this regard. Certain mass separation methods act as "mass filters". For example, the quadrupole mass spectrometer only permits ions with a particular mass charge ratio to pass through at any one time. This means that a considerable proportion of ions never reaches the detector. Most mass spectrometers detect only one part of the mass spectrum at a time. Given that a large proportion of the mass spectrum may be empty or irrelevant but is usually scanned anyway, this means a further large proportion of the sample is wasted. These factors may be a problem in detecting very low abundances of ions but these problems can be overcome in large part by correct configuration of the instrumentation.

To ensure better quantification one could attempt to ensure that all ions are detected. Mattauch-Herzog geometry sector instruments permit this but have a number of limitations. Sector instruments are organised into distinct regions (sectors) that perform certain functions. In general, ions generated in an ion source from a divergent beam, which is narrowed by passage through adjustable slits. This defined beam then passes through a field free region into an electric sector, which focusses it. The passage through the slits results in some loss of ions and therefore results in a reduction in sensitivity to the sample. The focussed ion beam passes through a second field-free region and on into a magnetic sector. This last sector focusses the beam on the basis of the mass-to-charge ratios of the ions. A photographic plate can be placed across the mass-separated beam split can be used to measure the abundancies of ions and their mass-to-charge ratios. Unfortunately, the photograph plate has only a small dynamic range of sensitivity before becoming saturated and is cumbersome. Better dynamic range is achievable by use of electron multiplier arrays but at a cost of some loss in resolution. By use of such an array, a family of well-characterised mass labels could be monitored. In general, array detectors would allow the simultaneous and continuous monitoring of a number of regions of the mass spectrum. The array limit on the resolution of closely spaced regions of the spectrum might restrict the number of labels one might use. For 'selected ion monitoring' (SIM), the quadrupole assembly has an advantage over many configurations in that the electric fields that separate ions of different mass-to-charge ratios can be changed with extreme rapidity, allowing a very high sampling rate over a small number of peaks of interest.

Mass Analyser Geometries

Mass spectrometry is a highly diverse discipline an numerous mass analyser configurations exist and which can often be combined in a variety of geometries to permit analysis of complex organic molecules. Typical single stage mass analysers are quadrupoles or time-of-flight instruments, which are both compatible with this present invention. Sector instruments are also applicable.

Orthogonal TOF Mass Spectrometry

For biological applications sensitivity and quantification of samples are very important. An approach that is comparable in sensitivity to array geometries is the orthogonal time-of-flight mass spectrometer. This geometry allows for very fast sampling of an ion beam followed by almost instantaneous detection of all ion species. The ion current leaving the source, probably an electrospray source for many biological applications, passes a flat electrode placed perpendicular to the beam. This electrode is essentially an electrical gate. A pulsed electrical potential deflects part of the ion beam 'orthogonally' into a time-of-flight mass analyser. When the electrical gate is 'closed' to deflect ions into the TOF analyser, a timer is triggered. The flight time of the deflected ions is recorded and this is sufficient to determine their mass-to-charge ratios. The gate generally only sends a short pulse of ions into the TOF analyser at any one time. Since the arrival of all ions is recorded and since the TOF separation is extremely fast, the entire mass spectrum is measured effectively simultaneously. Furthermore, the gate electrode can sample the ion beam at extremely high frequencies so that multiple spectra can be accummulated in a very short time interval. This is important where the sample concentration in the ion source is low or lasts for only a short time. The orthogonal TOF geometry is very sensitve.

Analysis of Mass Labelled Nucleic Acids by Tandem Mass Spectrometry

Tandem mass spectrometry describes a number of techniques in which ions from a sample are selected by a first mass analyser on the basis of their mass-to-charge ratios for further analysis by induced Fragmentation of those selected ions. The fragmentation products are analysed by a second mass analyser. The first mass analyser in a tandem instrument acts as a filter in selecting ions that are to be investigated. On leaving the first mass analyser, the selected ions pass through a collision chamber containing a neutral gas, resulting in some of them fragmenting.

ION SOURCE→MS1→COLLISION CELL→MS2→ION DETECTOR

Induced Cleavage of Mass Labels

Various analytical techniques have been developed over the years to promote fragmentation of ions for use in structural studies and for unambiguous identification of molecules on the basis of fragmentation "fingerprints". Most ionisation techniques cause some fragmentation but soft ionisation methods produce few fragment ions. However, variations on, for example, chemical ionisation techniques can be used to aid fragmentation. Similarly, electrospray ionisation can be modified slightly to promate fragmentation including a corona discharge electrode so as to ionise more sample molecules or to increase fragmentation of molecular ions. This technique has been termed Atmospheric Pressure Chemical Ionisation (APCI).

A more active approach to fragmentation entails inducing decomposition of molecular ions as, for example, by collision induced decomposition (CID). CID uses mass spectrometer constructions to separate out a selected set of ions and then to induce their fragmentation by collision with a neutral gas; the resulting fragment ions are analysed by a second mass spectrometer.

Other induced cleavage techniques are compatible with mass labelling methodologies. One preferred method, as discussed earlier, is photon induced decomposition, which involves the use of photocleavable mass labels. A typical geometry uses a tandem mass analyser configuration similar to those used in CID, but the collision cell is replaced by a photo-excitation chamber in which the ion stream leaving the first mass analyser is irradiated by laser light. High intensity lasers are required to ensure that a significant proportion of a fast moving ion stream interacts with a photon appropriately to induce cleavage. The positioning of the laser is extremely important to ensure exposure of the stream for a significant period of time. Tuning the laser to a specific frequency allows for precise control over the bonds that are induced to cleave. Thus, mass labels linked with an appropriate photocleavable linker to their probes can be cleaved within the mass spectrometer. The photocleavage stage does not require a tandem geometry, the photocleavage chamber could be within or immediately following the ion source.

A further possible technique for fragmenting molecular ions is surface induced decomposition. Surface induced decomposition is a tandem analyser technique that involves generating an ion beam which is separated in a first analyser into selected m/z ratios. Any selected ions are collided with a solid surface at a glancing angle. The resulting collision fragments can then be analysed by a second mass spectrometer.

One type of tandem mass spectrometer utilises a triple quadrupole assembly, which comprises three quadrupole mass analysers, one of which acts as a collision chamber. The collision chamber quadrupole acts both as a collison chamber and as an ion guide between the two other mass analyser quadrupoles. Gas can be introduced into the middle quadrupole to allow so that its molecules collide with the ions entering from the first mass analyser. Fragment ions are separated in the third quadrupole. Induced cleavage can be performed with geometries other than those utilising tandem sector or quadrupole analysers. Ion trap mass spectrometers can be used to promote fragmentation through introduction of a buffer or 'bath' gas into the trap. Any trapped ions collide with buffer gas molecules and the resulting energy transfer may lead to collision. The energy of collision may be increasd by speeding up the trapped ions. Helium or neon may be used as the bath gas in ion traps. Similarly, photon induced fragmentation could be applied to trapped ions. Another favorable geometry is a Quadrupole/Orthogonal Time-of-Flight instrument, in which the high scanning rate of a quadrupole is coupled to the greater sensitivity of a TOF mass analyser to identify products of fragmentation.

Conventional 'sector' instruments are another common geometry used in tandem mass spectrometry. A sector mass analyser comprises two separate 'sectors', an electric sector which focusses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. This geometry might be quite effective for cleaving labels from a mass labelled nucleic acid. Two complete sector mass analysers separated by a collision cell can also be used for analysis of mass labelled nucleic acids.

Ion Traps

Ion Trap mass spectrometers are a relative of the quadrupole spectrometer. The ion trap generally has a 3 electrode construction—a "torroidal" electrode and 'cap' electrodes at each end forming a cavity (the ion trap). A sinusoidal radio frequency potential is applied to the cylindrical electrode while the cap electrodes are biased with DC or AC potentials. Ions injected into the cavity are constrained into a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass-to-charge ratio by altering the oscillating radio frequency potential. The ejected ions can then be detected allowing a mass spectrum to be produced.

Ion traps are generally operated with a small quantity or a 'bath gas', such as helium, present in the ion trap cavity. This increases both the resolution and the sensitivity of the device as the ions entering the trap are essentially cooled to the ambient temperature of the bath gas through collision with its molecules. Collisions dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving greater resolution.

Ion traps can mimic tandem sector mass spectrometer geometries. In fact, they can mimic multiple mass spectrometer geometries thereby allowing complex analyses of trapped ions. A single mass species from a sample can be retained in a trap, viz., all other species can be ejected. Then, the retained species can be carefully excited by superimposing a second oscillating frequency on the first. The kinetically-excited ions collide with bath gas molecules and will fragment if sufficiently excited. The fragments can be analysed further. This is MS/MS or MS². A fragment ion can be further analysed by ejecting all other ions and then kinetically exciting the fragment so that it fragments after collison with bath gas molecules (MS/MS/MS or MS³). This process can be repeated for as long as sufficient sample exists to permit further analysis (MS"). It should be noted that ion traps generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but, in FTICR MS, the ions are trapped in a high vacuum chamber (ICR cell) by crossed electric and magnetic fields. The electric field is generated by a pair of plate electrodes that form two sides of a box. The box is contained in the field of a magnet, which in conjunction with the two plates (the trapping plates), constrain injected ions to have a cycloidal trajectory. The ions may be kinetically excited into larger cycloidal orbits by applying a radiofrequency pulse to two 'transmitter plates'. The cycloidal motions of the ions generate corresponding electric fields in the remaining two opposing sides (plates) of the box, which comprise the 'receiver plates'. The excitation pulses kinetically excite ions into larger orbits, which decay as the coherent motions of the ions is lost through collision with neutral gas molecules. The corresponding signals detected by the receiver plates are converted to a mass spectrum by Fourier transform analysis. For induced fragmentation experiments these instruments can act in a similar manner to an ion trap—all ions except a single species of interest can be ejected from the ICR cell. A collision gas can be introduced into the trap and fragmentation can be induced. The fragment ions can be analysed subsequently. Generally, fragmentation products and bath gas combine to give poor resolution if analysed by FT of signals detected by the 'receiver plates'. However, the fragment ions can be ejected from the cell and then analysed in a tandem configuration with, for example, quadrupole.

Mass Labelled Hybridisation Probes

To acheive the required behaviour from a mass label, certain chemical properties are desirable. These are represented in particular molecular groups or moieties that can be incorporated into mass labels in a number of ways.

Structure of Mass Labelled Hybridisation Probes

Mass labelled hybridisation probes may have the following basic structures.

Nu-M

Nu-L-M

Where Nu is a nucleic acid probe and L is a linker group connecting the nucleic acid probe to the mass label, M. The linker group (L) is optional and the mass label may have the necessary linker features incorporated into it. The linker group is not necessary when a non-cleavable mass-labelled hybridisation probe is required. Nucleic acids are linear polymers of nucleotides, of which there is a relatively small number of naturally occurring species but a growing number of chemically synthesised analogues, which can be coupled to the linker group at numerous positions. Such possibilities are discussed later.

Linkers

Linker groups may have the following structural features: Handle 1—[cleavable group]—Handle 2 The handles 1, 2 are chemical groups allowing one end of the linker to be coupled to the nucleic acid probe and the other to the mass label. At least one cleavable group is required between or as part of the handles to allow the mass label to be controllably removed from its associated nucleic acid probe.

Mass Labels

Mass labels may have the following structure: Handle— Mass Label Where the handle is a group permitting the mass label to be coupled to its corresponding nucleic acid probe or to the linker between the mass marker and its nucleic acid probe.

Properties of Mass Labels

For optimum performance using present mass spectrometric techniques, a mass-to-charge ratio of up to 2000 to 3000 units is a suitable range for such mass labels as this corresponds to the range over which singly charged ions can be detected reliably at greatest sensitivity. However, labels of mass less than 200 to 300 daltons are not ideal because the low mass end of any mass spectrum tends to be populated by solvent molecules, small molecule impurities, multiple ionisation peaks and fragmentation peaks. Further, each label should be separated by a minimum of about 4 daltons from its neighbours to avoid overlap caused by carbon, nitrogen and oxygen isotope peaks.

The mass label should ionise and separate so as to form predominantly one species (without fragmentation).

The mass label should be easily ionised to ensure that as much of the cleaved mass label as possible is detected.

To permit detection labels need to have a net electric charge, but preferably should not be multiply ionised, i.e. they should have a single electric charge. Furthermore, the labels should be resistant to fragmentation so that each peak in a mass spectrol scan corresponds only or uniquely to a single label; this simplifies analysis of the data and reduces any ambiguity in the determination of the quantity of the label, a criterion which is very important for some of the applications for which this invention has been developed.

Various chemical functionalities exist, which carry or could carry positive charges for positive ion mass spectrometry. These include but are not limited to amines (particularly tertiary amines and quaternary amines), phosphines and sulphides. Quaternary ammonium groups carry a single positive charge and do not require further ionisation. For positive ion mass spectrometry these pre-ionised species allow great sensitivity. Hence, preferred positive ion mass labels should carry at least one such group. Crown ethers form another class of compound which could be used to carry positive charges.

Various chemical functionalities are available to carry a negative charge for negative ion mass spectrometry and include, but are not limited to, carboxylic, phosphonic, phosphoric and sulphonic acids, phenol hydroxyls, sulphonamides, sulphonylureas, tetrazoles and perfluoroalcohols.

Ionisation and Separation of Mass Labels From Nucleic Acid Probes

DNA and other nucleic acids tend to fragment to extensively in a mass spectrometer. It is desirable to ensure DNA fragment peaks in the resulting mass spectrum do not obscure those arising from mass labels. It is preferable to ensure that nucleic acid probe fragments are separated from mass labels after cleavage. To this end, one can use mass labels that form negative ions on ionisation and which can be separated by negative ion spectrometry. Nucleic acids, despite having a negatively charged backbone, have a tendency to be protonated on ionisation, particularly by electrospray and related liquid-to-gas phase ionisation techniques. This means that, if the mass spectrometer is configured for negative ion spectrometry, only negatively charged mass labels should appear in the mass spectrum. Most nucleic acid fragments will not reach the detector.

If such an approach is taken, protonation of nucleic acid probes can be promoted through the use of appropriate buffer solutions, thus ensuring that nucleic acids are extensively present with a pre-existing positive charge.

Fragmentation Within the Mass Spectrometer

Fragmentation is a highly significant feature of mass spectrometry. With respect to this invention it is important to consider how a mass label is to be identified. At the one extreme mass labels may be designed such that they are highly resistant to fragmentation and the label is identified by the appearance of the label's molecular ion in the mass spectrum. In this situation, families of labels having unique molecular ions would need to be designed. At the other extreme, a mass label having a highly characteristic fragmentation pattern could be designed such that this pattern would identify it. In this case, families of labels having non-overlapping patterns or with at least one unique fragmentation species for each label must be designed. Fragmentation is a property of the initial molecule and of the ionisation technique used to generate the ions from it. Different techniques impart differing amounts of energy to the initially formed ion and the chemical environment of the ions vary considerably. Thus, labels that are appropriate for one mass spectrometric technique may be inappropriate in another. The preferred approach is to design fragmentation-resistant molecules, although some fragmentation is inevitable. This means one aims to identify molecules with a single major species, which may be either the molecular ion or a single easily produced fragment ion.

Determination of Bond Stability in a Mass Spectrometer

In neutral molecules it is reasonably simple to determine whether a molecule is resistant to fragmentation, by consideration of bond strengths. However, when a molecule is ionised, bond strengths may increase or decrease in ways that are difficult to predict a priori. For example, for a given a bond, X-Y, in its un-ionised form:

$$X-Y \rightarrow X^\circ + Y^\circ \text{ and,}$$

$$\therefore D(X-Y) = \Delta H(X^\circ) + \Delta H(Y^\circ) - \Delta H(X-Y)$$

in which D represents the bond dissociation energy in suitable units.

But, for an ionised species (positive in this example), $$D(X-Y)^+ = \Delta H(X^+) + \Delta H(Y^\circ) - \Delta H(X-Y^+)$$

$$\therefore D(X-Y) - D(X-Y)^+ = \Delta H(X^+) - \Delta H(X^+) - \Delta H(X-Y) - \Delta H(X-Y^+)$$

Because $$I(X^\circ) = \Delta H(X^+) - \Delta H(X^\circ), \text{ where is the ionisation energy,}$$

$$I(X-Y) = \Delta H(X-Y^+) - \Delta H(X-Y)$$

and, $\therefore D(X-Y) - D(X-Y)^+ = I(X-Y) - I(X^\circ)$

This means that $D(X-Y) - D(X-Y)^+ > 0$, it $I(X-Y) > I(X^\circ)$ but,

Similarly, $D(X-Y) - D(X-Y)^+ < C$, if $I(X-Y) < I(X^\circ)$

Because both (X–Y) and I(X°) are positive, a stronger bond results if $I(X-Y) < I(X^\circ)$ and a weaker bond arises in the ion of $I(X-Y) > I(X^\circ)$ In the equations above, D(A–B) refers to bond dissociation energy of the species in parentheses, I(N) refers to the ionisation energy of the species in parentheses and ΔH is the enthalpy of formation of the species in parentheses. For present purposes, $\Delta S \cong 0$ and therefore, $\Delta G \cong \Delta H$. The upshot of the equations above is that in order to predict whether a bond is likely to be stable under a given set of ionisation conditions it is necessary to know the ionisation energy of the molecule and the ionisation energy of the neutral fragment that results from fragmentation of the bond in question.

For example, consider the C—N bond in aniline:

$I(NH_2.) = 11.14$ electronvolts(eV) and $I(C_6H_5NH_2) = 7.7$ eV
$\therefore I(C_6H_5NH_2) < I(NH_2^\circ)$ by 3.44 eV The alternative cleavage at this bond is:

$I(C_6H_5^\circ) = 9.35$ eV and $I(C_6H_5NH_2) = 7.7$ eV $I(C_6H_5NH_2) < I(C_6H_5)$ by 1.65 eV Therefore, this bond is thus not easily broken in the ion. Aniline, if it has sufficient initial energy to fragment, is generally observed to cleave by releasing HCN, rather than by cleavage of a C—N bond. Similarly considerations apply to phenol:
$I(OH^\circ) = 13$ eV and $I(C_6H_5OH) = 8.47$ eV $\therefore I(C_6H_5OH) < I(OH^\circ)$ by 4.53 eV The alternative cleavage at this bond is $I(C_6H_5^\circ) = 9.35$ eV and $I(C6H_5OH) = 8.47$ eV
$\therefore I(C_6H_5OH) < I(C_6H_5^\circ)$ by 0.88 eV C—O bond cleavage is not observed in the positive molecular ion from phenol.

Determining the differences in ionisation energies of molecules and neutral fragments is a general working principle, which can be used to predict likely ionic bond strengths. If the energy added during ionisation is less than the ionic bond strength then fragmentation will not be observed. Typical ionic bonds that have good strength include, aryl-O, aryl-N, aryl-S bonds which are stabilised by delocalisation of electrons. Generally, aliphatic type bonds become less stable in ionic form. Thus single C-C bonds are weak in ions but C=C is still relatively strong. Aryl-C=C tends to be strong too for the same reasons as aryl-O, etc. Aryl or Aryl-F bonds are also strong in ions which is attractive for mass labelling as fluorocarbons are cheap to manufacture, are chemically inert, have a detectable mass defect with respect to hydrocarbon molecules and fluorine has only the single naturally-occurring isoptope, 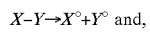F.

Similar considerations apply to negative ions, except that electron affinities need to be used in the above equations.

Properties of Linkers

Controllable release of mass labels from their associated nucleic acid probe can be effected in a variety of ways:
Photocleavage
Chemical cleavage
Thermal cleavage
Induced Fragmentation within the mass spectrometer.

Figure 5:
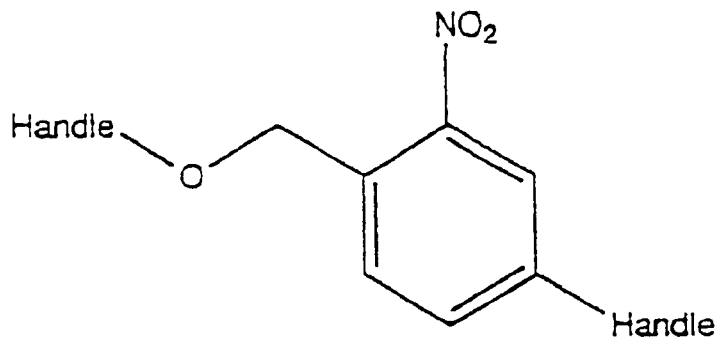
FIG. 5 shows photocleavable linkers suitable for use in the present invention.
Figure 5:
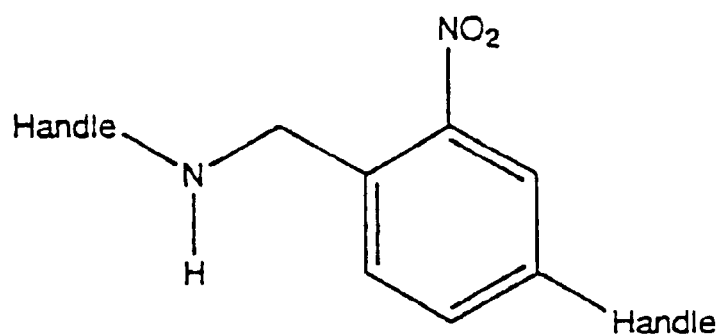

Photo-cleavable and chemically-cleavable linkers can be easily developed for the applications described. FIG. 5 shows a series of exemplary photocleavable linkers.

Ortho-nitrobenzyl groups are well known in the art as photocleavable linkers, cleaving at the benzylamine bond. For a review on cleavable linkers see reference 18, which discusses a variety of photocleavable and chemically-cleavable linkers.

Figure 6:
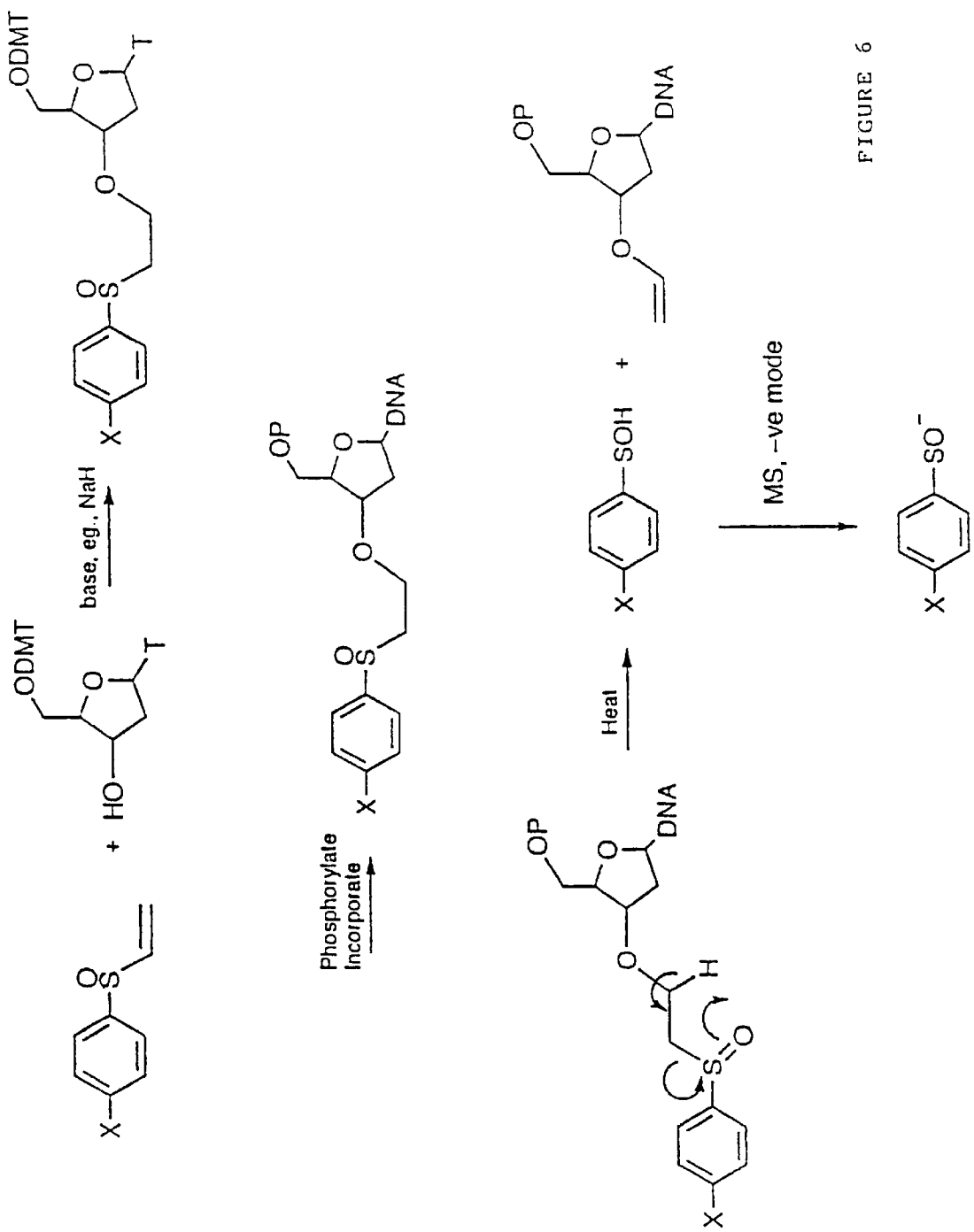
FIG. 6 shows a reaction scheme for production of mass labelled bases for use in the present invention.

Thermal cleavage operates by thermally induced rearrangements. FIG. 6 shows the synthesis of one example of a mass label linked via a thermally cleavable linker to the 3'-OH position of a thymidine residue. FIG. 6 also shows the thermally induced rearrangement that would cleave the label from its associated nucleotide. Clearly the group X in this example could be an aryl ether polymer, as discussed later. Advantageously, this thermally cleavable group also produces abundant negative ions suitable for negative ion mass spectrometry. Thermolysis of this molecule requires the S=O group in the linker. Here, S could be replaced with N or C, and O be replaced by S. For further examples see reference 28.

Cleavage of Mass Labels Within the Mass Spectrometer

A preferred method of cleavage is through the use of the ionisation process to induce fragmentation of labels. A linker may be designed to be highly labile in the ionisation process, such that it will cleave when the molecule to which it is attached is ionised in a mass spectrometer. There are two factors to consider in controlling cleavage using this method: (1) how much excess of energy is deposited in the ion during the ionisation process and, (2) whether this excess is sufficient to overcome any one bond energy in the ion. The excess of energy deposited is strongly determined by the ionisation technique used. In order for the deposited energy to effect cleavage of a bond the energy must be in a vibrational/rotational mode and must be sufficient to overcome the dissociation energy of the bond. The bond energy is obviously determined by the chemical structure of the molecule being analysed. Bond energies are discussed later. Generally speaking, energy is imparted as electronic, vibrational, rotational and translational energy in the ionisation process. Within a very short time of ionisation, most of this excess of internal energy will have transformed into vibrational and rotational energy by intersystem and interstate crossing. The excess of internal revibrational energy may or may not lead to bond scission. In order impart more internal vibrational energy into the moving ions, they can be collided with a bath gas to give fragmentation of the ion. In an electrospray source there is a bath gas and volatised solvent. Ions can be accelerated through an electric field to increase the energy of collision with a bath gas. The acceleration kinetic energy to the ions. If sufficient kinetic energy is imparted to the ions then collisions with the bath gas will result in fragmentation of the ions. The amount of kinetic energy required depends on the strength of the bonds in the ion but the amount of energy imparted can be controlled by regulating the accelerating potential.

Figure 7:
FIG. 7 shows fragmentable linkers suitable for use in the present invention.
Figure 7:
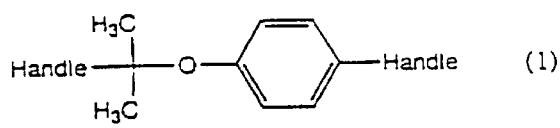
Figure 7:
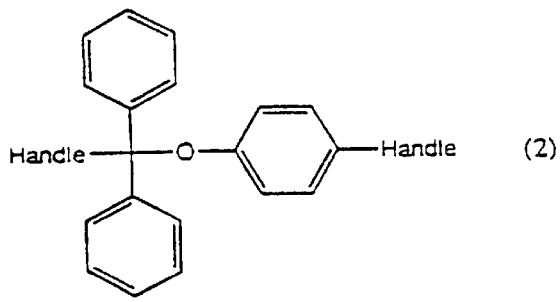
Figure 7:
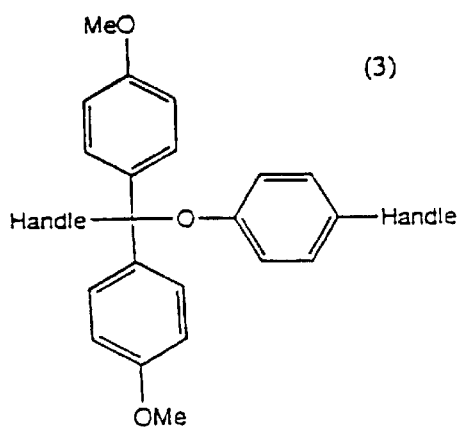
Figure 7:
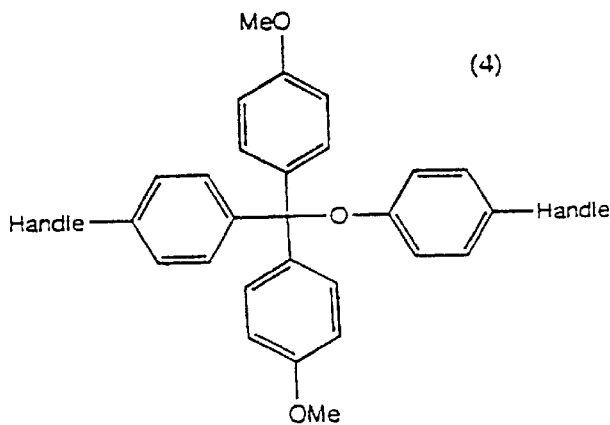

For the purposes of generating a linker for mass labels that cleaves at a predetermined bond during ionisation, there needs to be a single weak bond in the linker with the remainder being strong ones. Certain groups are particularly resistant to fragmentation, while others such as aliphatic type bonds, are reasonably susceptible to cleavage. In order to design a linker that cleaves at a specified location, a molecule might be designed that is broadly resistant to fragmentation but, which contains a 'weak link'. Certain structural features are found to stabilise fragment ions when cleavage occurs at certain bonds in an ion. Linear alkanes fragment relatively randomly while molecules containing secondary and tertiary alkyl groups cleave most commonly at the branching points of the molecule due to the increased stabilisation of secondary and tertiary carbocations. Similarly, double bonds stabilise adjacent positive or negative charges through resonance or delocalisation effects. Similar effects are noted in bonds adjacent to aryl groups. Some cleavable linkers that can be induced to fragment by collision or otherwise are shown in FIG. 7. These are numbered in order of their increasing lability. The groups on the left of the cleavable bond are well known as good leaving groups and are used to protect reactive positions in a molecule. As such they will be susceptible to chemical cleavage under certain conditions. The precise structure that might be chosen would depend on the application and the chemical environment of the probe. Linker (4) in FIG. 7 is highly susceptible to protic chemical attack and so would only be usable as a fragmentable linker if the probing reaction reaction was not acidic. Linker (1) is considerably less photolytically cleavable. Obviously, these groups could be chosen intentionally to cleave chemically as required. It is easy to see from FIG. 7 that these linkers can also form part of a delocalised aryl-ether polymer system. The group to the right of the cleavable bond essentially stabilises a negative charge, which is advantageous in that it promotes bond breakage at this site and can provide a detectable negative ion. Other charge stabilising groups could be used at this position. The 'handles' on this and other Figures generally represents a reactive group useful in the synthesis of the mass labelled base sequence, which may not be present in the mass labelled molecule as synthesised.

Nucleic Acid Probes

Linking Groups to Nucleic Acids

Mass labels and their linkers can be attached to a nucleic acid at a number of locations. For conventional solid phase synthesisers the 5' hydroxyl of the ribose sugar is the easiest to derivitise. Other favoured positions for modifications are on the base at the 5' position in pyrimidines and the 7' and 8' positions in purines. These would be the preferred positions to attach cleavable mass labels and non-cleavable mass labels.

The 2' position on the sugar is accessible for mass modifications but is more appropriate for small mass modifications that are not to be removed.

The phosphate linkage in natural nucleic acids can be modified to a considerable degree as well, including derivitisation with mass labels.

Hybridisation Probes

Depending on the application, modified nucleic acids might want to be used, which contain a number of different analogues for which hybridisation behaviour is modified. This is particulary important when groups of hybridisation probes are used simultaneously. It may be desirable to modify the hybridisation behaviour of a group of probes so that the melting temperatures of the correctly hybridised probes are very close to or at least above some threshold. Preferably the melting temperature of incorrectly hybridised probes will fall below this threshold. This allows groups of probes to be used simultaneously whilst ensuring the stringency of hybridisation reactions.

There are major differences between the stability of short oligonucleotide duplexes containing all Watson-Crick base pairs. For example, duplexes comprising only adenine and thymine are unstable relative to duplexes containing only guanine and cytosine. These differences in stability can present problems when trying to hybridise mixtures of short oligonucleotides to a target RNA. Low temperatures are needed to hybridise A-T rich sequences but at these temperatures G-C rich sequences hybridise to sequences that are not fully complementary. This means that some mismatches may happen and specificity can be lost for the G-C rich sequences. At higher temperatures G-C rich sequences hybridise specifically but A-T rich sequences do not hybridise.

In order to normalise these effects modifications can be made to nucleic acids. These modifications fall into three broad categories: base modifications, backbone modifications and sugar modifications.

Base Modifications

Numerous modifications can be made to the standard Watson-Crick bases. The following are examples of modifications that should normalise base pairing energies to some extent but they are not limiting:

- The adenine analogue, 2,6-diaminopurine, forms three hydrogen bonds to thymine rather than two and therefore forms more stable base pairs.
- The thymine analogue, 5-propynyldeoxyuridine, forms more stable base pairs with adenine.
- The guanine analogue, hypoxanthine, forms two hydrogen bonds with cytosine rather than three and therefore forms less stable base pairs.

These and other possible modifications should make it possible to compress the temperature range at which short oligonucleotides can hybridise specifically to their complementary sequences.

Backbone Modifications

Nucleotides may be readily modified in the phosphate moiety. Under certain conditions, such as low salt concentration, analogues such as methylphosphonates, triesters and phosphoramidates have been shown to increase duplex stability. Such modifications may also have increased nuclease resistance. Further phosphate modifications include phosphodithirates and boranophosphates, each of which increases the stability of oligonucleotide against exonucleases.

Isosteric replacement of phosphorus by sulphur gives nuclease resistant oligonucleotides (see reference 19). Replacement by carbon at either phosphorus or linking oxygen is also a further possibility.

Sugar Modifications

Various modifications to the 2' position in the sugar moiety may be made (see references 20 and 21). The sugar may be replaced by a different sugar such as hexose or the entire sugar phosphate backbone can be entirely replaced by a novel structure such as in peptide nucleic acids (PNA). For a discussion see reference 22. PNA forms duplexes of the highest thermal stability of any analogues so far discovered.

Hydrophobic Modifications

Addition of hydrophobic groups to the 3' and 5' termini of an oligonucleotide also increase duplex stability by excluding water from the bases, thus reducing 'fraying' of the complex, i.e. hydrophobic groups reduce solvation of the terminal bases.

Artificial Mismatches

One major source of error in hybridisation reactions is the stringency of hybridisation of the primers to the target sequence and to the unknown bases beyond. If the primers designed for a target bear single artificially introduced mismatches the discrimination of the system is much higher (see reference 23). Additional mismatches are not tolerated to the same extent that a single mismatch would be when a fully complementary primer is used. It is generally found that the difference in melting temperature between a duplex with one mismatch and a duplex with two mismatches is greater than the difference between a correctly hybridised duplex and a duplex containing a single mismatch. Thus this would be anticipated as being an important feature of the hybridisation probes disclosed in this application. If a nucleic acid probe has a critical base, i.e. to detect a Single Nucleotide Polymorphism, an artificial mismatch, introduced 1 helical turn away from the critical base destabilises the double helix to a considerable degree if there is a second mismatch at the probe site.

Hybridisation Protocols

Details of effects on hybridisation conditions, particularly those of buffers and temperature, for nucleic acid probes can be found in be found in references 24 to 26.

Oligonucleotide Synthesis

Methods of synthesis of oligonucleotides are well known in the art (see references 27 and 28).

Mass Label Synthesis

For any practically or commercially useful system it is important that construction of labels be as simple as possible using as few reagents and processing steps as possible. A combinatorial approach in a which a series of monomeric molecular units is available to be used in multiple cominations with each other would be ideal.

One can synthesise mass labels using organic chemistry techniques. Such labels might carry a single charge bearing group and should be resistant to fragmentation in the mass spectrometry technique used. Amine derivatives, quaternary ammonium ions or positive sulphur centres are good charge carriers if positive ion mass spectrometry is used. These have extremely good detection properties that generate clean sharp signals. Similarly, negatively charged ions can be used, so molecules with carboxylic acid, sulphonic acid and other moieties are appropriate for negative ion spectrometry. Labels for MALDI mass spectrometry can be generated by derivitising known molecules that are excitable by UV visible laser light, such as sinapinnic acid or cinnamic acid, of which a number of derivatives are already commercially available. Fragmentation resistant groups are discussed above.

For a text on organic chemistry see reference 29 or 30.

Combinatorial synthesis of such labels can be achieved in a relatively simple manner. Preferred mass label structures are shown below.

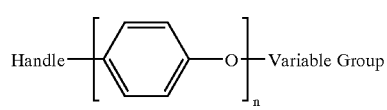

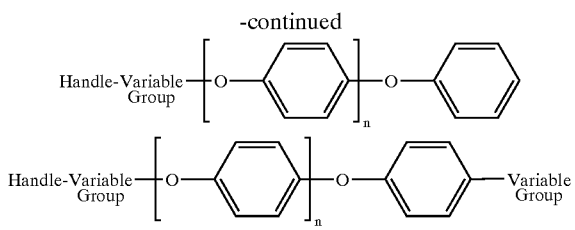

Figure 8:
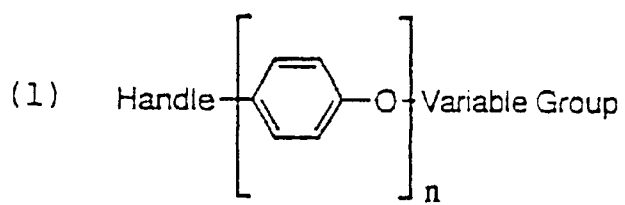
FIG. 8 shows mass label structures for use in the present invention.
Figure 8:
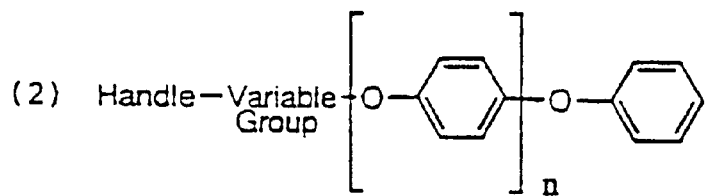
Figure 8:
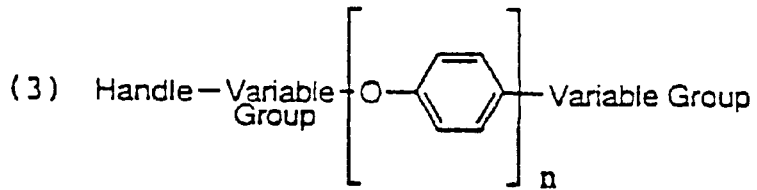
Figure 8:
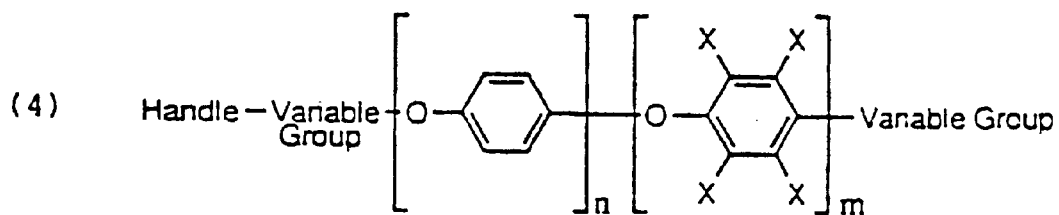
Figure 9:
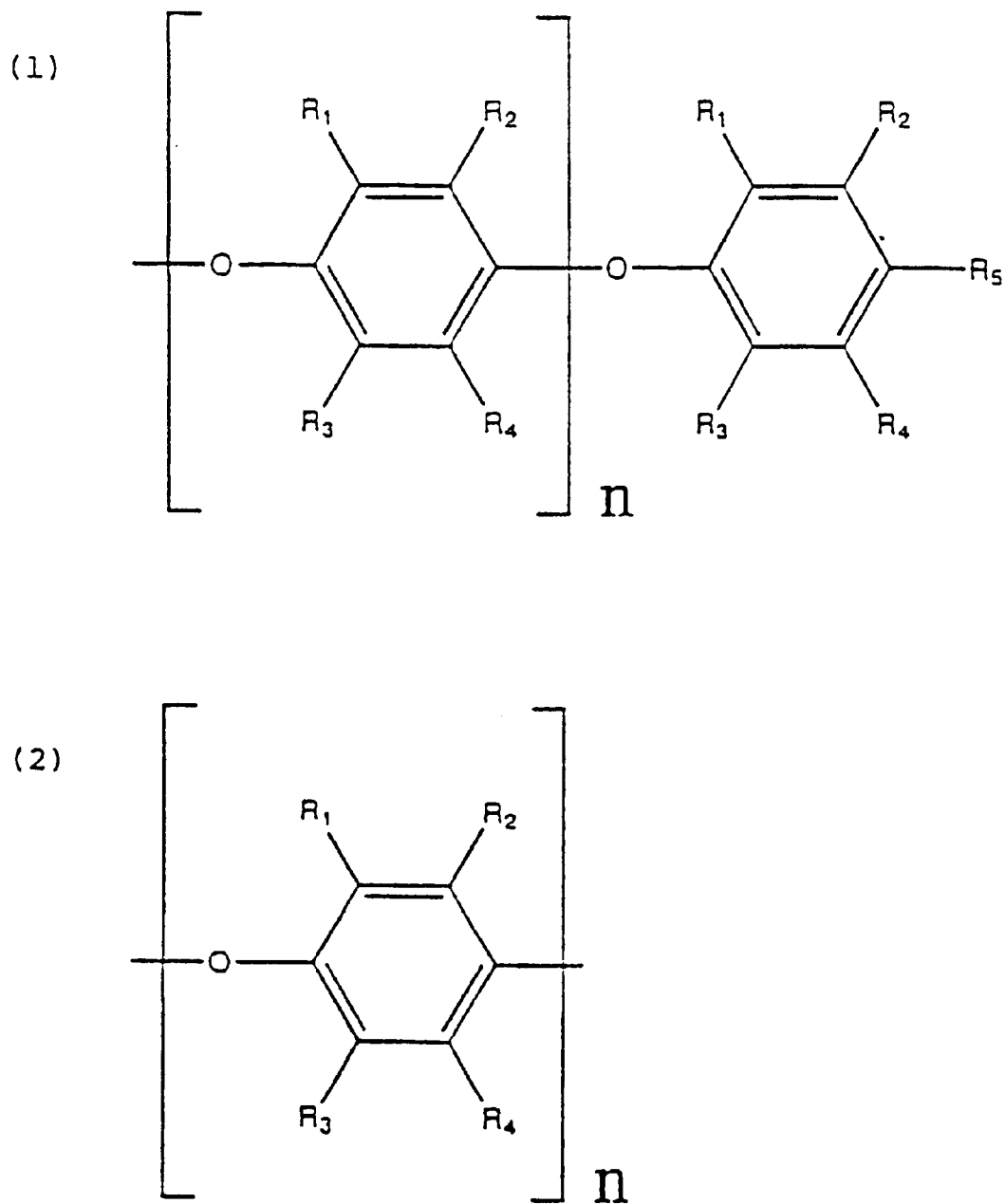
FIG. 9 shows variable groups and mass series modifying groups for use in the present invention.

These polyaryl ether structures are very resistant to fragmentation and produce good negative ions since the delocalisation of electrons over the molecule can effectively stabilise a negative charge. These molecules are also thermally stable and so are particularly compatible with thermally cleaved linkers and with linkers cleaved by collision processes within the mass spectrometer. The 'Variable Groups' at either end of the polyaryl ethers are preferrably substituted aryl ethers which modify the properties of the mass label (FIG. 9). Such modifying groups include 'mass series modifying' groups (see FIG. 9), solubilising groups, charge carrying groups (see FIG. 10) and mass defect groups (see FIG. 8). A linear polymer of polyaryl ethers increases in mass by 92 mass units with each additional "phenoxy" residue in the molecule. To exploit the mass spectrum fully, mass labels need only be about 4 daltons apart. To generate mass markers 4 daltons apart each mass label preferably contains a group that shifts the mass of each series of aryl ethers. This Mass Series Modifying group (MSM) (see FIG. 9) acts to offset each series of aryl-ether polymers from the others. With linear polymers of aryl ethers, each monomer of which adds 92 daltons, there will be no coincidence in mass for a maximum of 23 series if each series of mass markers is 4 mass units apart. In order to generate 256 mass labels, for example, one then needs to generate the 23 MSM groups, to link to polymers of aryl ethers with up to 12 consecutive phenoxy repeats. This would give a total of 276 mass labels.

Clearly a polymer, comprising a number of different subunits can be generated with those sub-units appearing in different sequences. Furthermore branched structures are also possible but only linear polymers are shown for convenience of illustration. The preferred structures shown are chosen for convenience of synthesis. Different sequences of the same subunits are not significantly more difficult to produce but it is preferable to generate as many labels as possible in as few synthetic steps as possible. A prefered synthesis strategy is to generate polyaryl ethers of up to twelve repeats and then deriviltise these with a number of different MSM groups, whose masses differ ideally by about 4 daltons to avoid overlap of isotope peaks. Variation in the MSM group can be fine-tuned by using isotopic substitutions; for example, replacement of 4 hydrogens in a molecule with 4 deuterium atoms gives a mass difference of 4 daltons.

Further examples of mass labels according to the present invention include aromatics, phenols, anilines and heteroanalogues thereof in monomeric, oligomeric or polymeric form and other moieties containing C=C or C≡C or heteroanalogues thereof as well as their oligomeric or polymeric counterparts. Molecules or moieties thereof containing C—H or C—hal (not F) bonds are to be avoided. In addition to the polyethers discussed above one can use as mass labels analogous thioethers, amines, phosphates, phosphonates, phosphorothioates, silanes, siloxanes, sulphorates, sulphonamides and those incorporating C=C, C≡C and C=N.

Where aromatics or heteroaromatics are used, they may be substituted or unsubstituted. If substituted, the substituents must also be resistant to fragmentation and may be selected from any of the categories set out above.

As discussed earlier, it is preferred that any mass label be resistant to fragmentation and should preferably have a stability to electron ionisation conditions at 50 volts.

An advantageous embodiment of this technology is the use of fluorinated mass labels when high resolution mass analysis of labels is employed after cleavage from their nucleic acid. A hydrocarbon molecule whose integral mass is 100, will have a fractionally higher accurate mass. In contrast, a fluorinated molecule whose integral mass is 100 has a fractionally lower accurate mass. These differences in mass are distinguishable in high resolution mass analysis and two molecules with the same integral mass but different compositions will produce distinct peaks in the mass spectrum if they have different degrees of hydro- and fluorocarbon. Fluorinated molecules are said to a have a 'mass defect'. Since fluorinated molecules are not common in living systems, this means that a fluorinated mass label will be distinguishable in the mass spectrum even in the presence of contaminating peaks due to fragmentation of the nucleic acids or from buffers as long as the nucleic acids and reagents used are not themselves fluorinated. Incorporation of a number of units of fluorinated aryl ethers is a simple means of introducing a mass defect into the mass label (see FIG. 8). An alternative to using a separate series of mass defect groups is to replace the polymers of normal aryl ethers wish their fluorinated analogues.

Amino Acids

With a small number of amino acids such as glycine, alanine and leucine, a large number of small peptides with different masses can be generated using standard peptide synthesis techniques well known in the art. With more amino acids many more labels can be synthesised. One does not need to be limited to natural amino acids. Either chiral form is acceptable and different non-natural side-chains are also acceptable. (see reference 31)

Example 1

Synthesis of a Negative Ion Forming Species
Materials

BSA (2-sulphobenzoic acid cyclic anhydride)—100 mg, 0.54 mmol

Benzyl alcohol—2 ml

Sodium Carbonate—1.1 equiv, 63 mg.

Method

Dissolve carbonate and BSA together and add benzyl alcohol. Warm to start reaction (CO2 evolved). Stir until effervescence ceases. Filter and precipitate product by the addition of diethyl ether. Stir for 10 minutes and isolate product by filtration. Product is a white solid. This molecule will be referred to as AG/1/75. (See FIG. 11).

Mass Spectrometry: Negative Ion Mode

Figure 11:
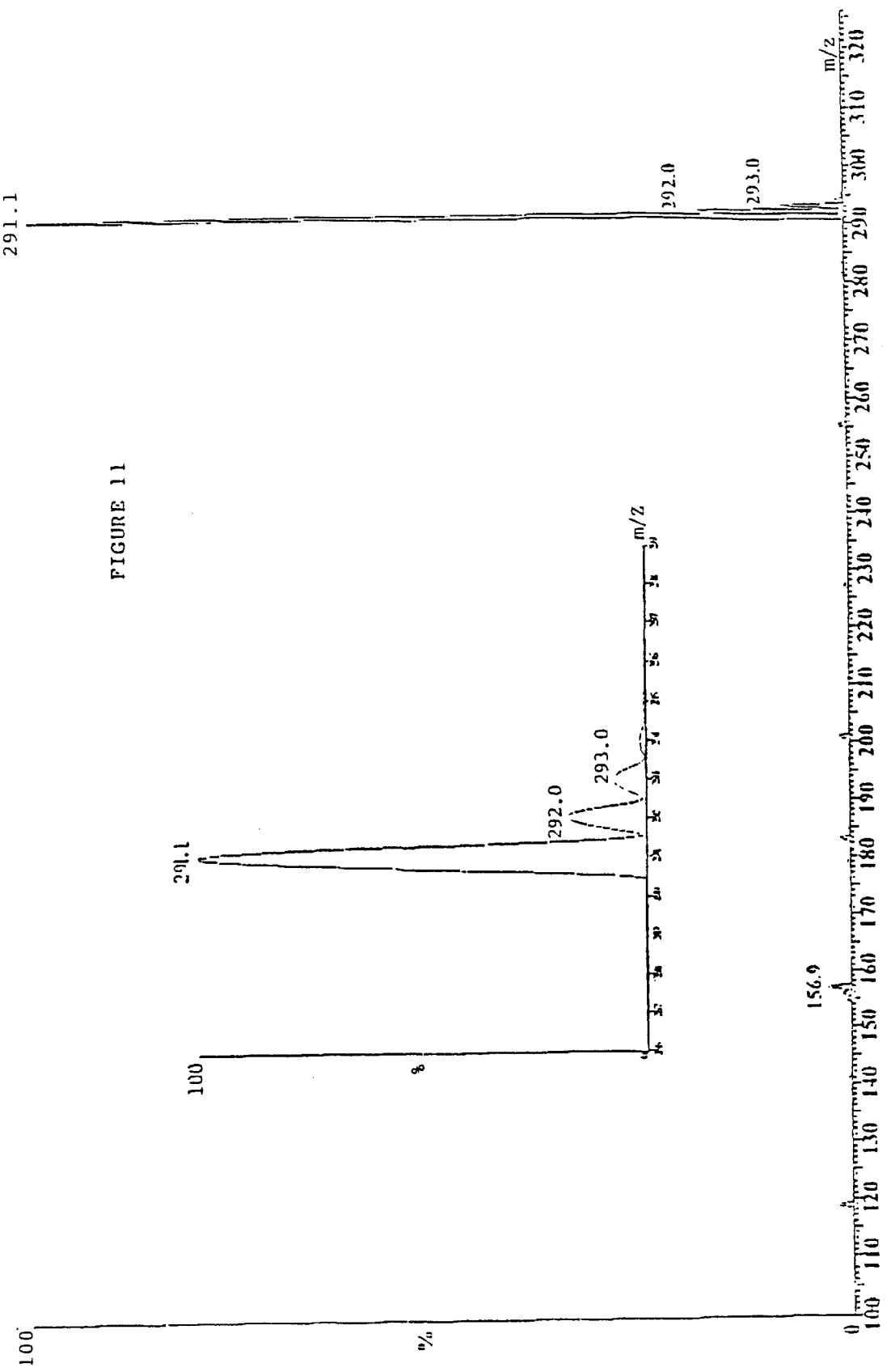
FIG. 11 shows a mass spectrum of model compound AG/1/75 in negative ion mode.

A negative ion mass spectrum of the previously synthesised molecule, AG/1/75 is shown in FIG. 11. This spectrum was generated with the molecule present at 10 ng/μl. The solvent was methanol and water in a 1:1 ratio. The spectrum was generated with an electrospray inlet system coupled to a scanning quadrupole mass spectrometer. The inset shows the mass peaks corresponding to the anion of AG/1/75 molecule, a singly charged negative ion at m/z 291 daltons [M–Na]⁻. Note that the isotope peaks are significant over about three daltons from the quasi molecular ion peak.

Figure 12:
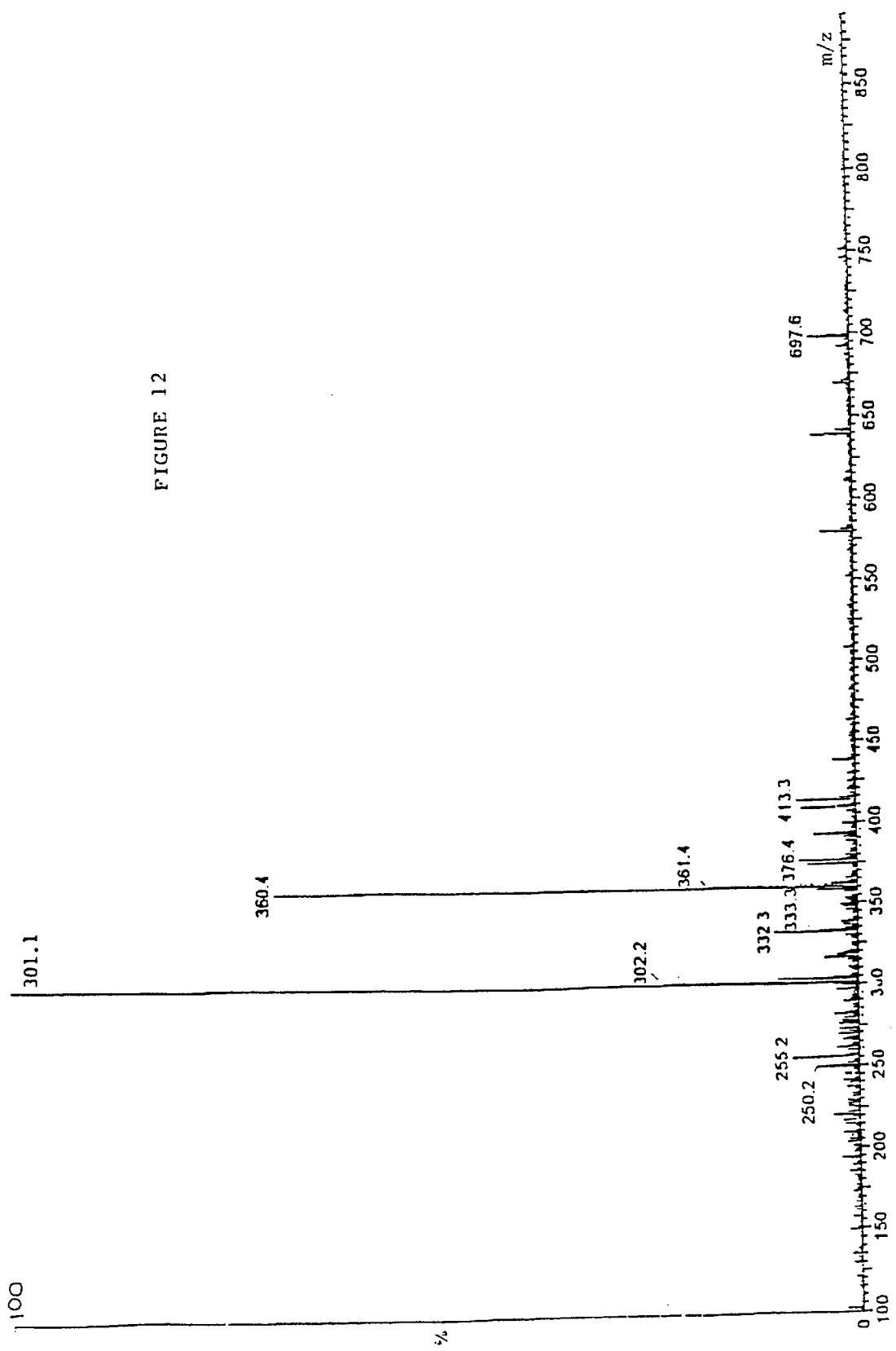
FIG. 12 shows a mass spectrum of model compound AG/1/75 in positive ion mode.

FIG. 12 shows a positive ion spectrum of AG/1/75. Where is no detectable molecular ion in this spectrum, hence this molecule is best used as a negative ion mode marker. Both of the above spectra were generated with a cone voltage in the electrospray source of 45 V.

Figure 13:
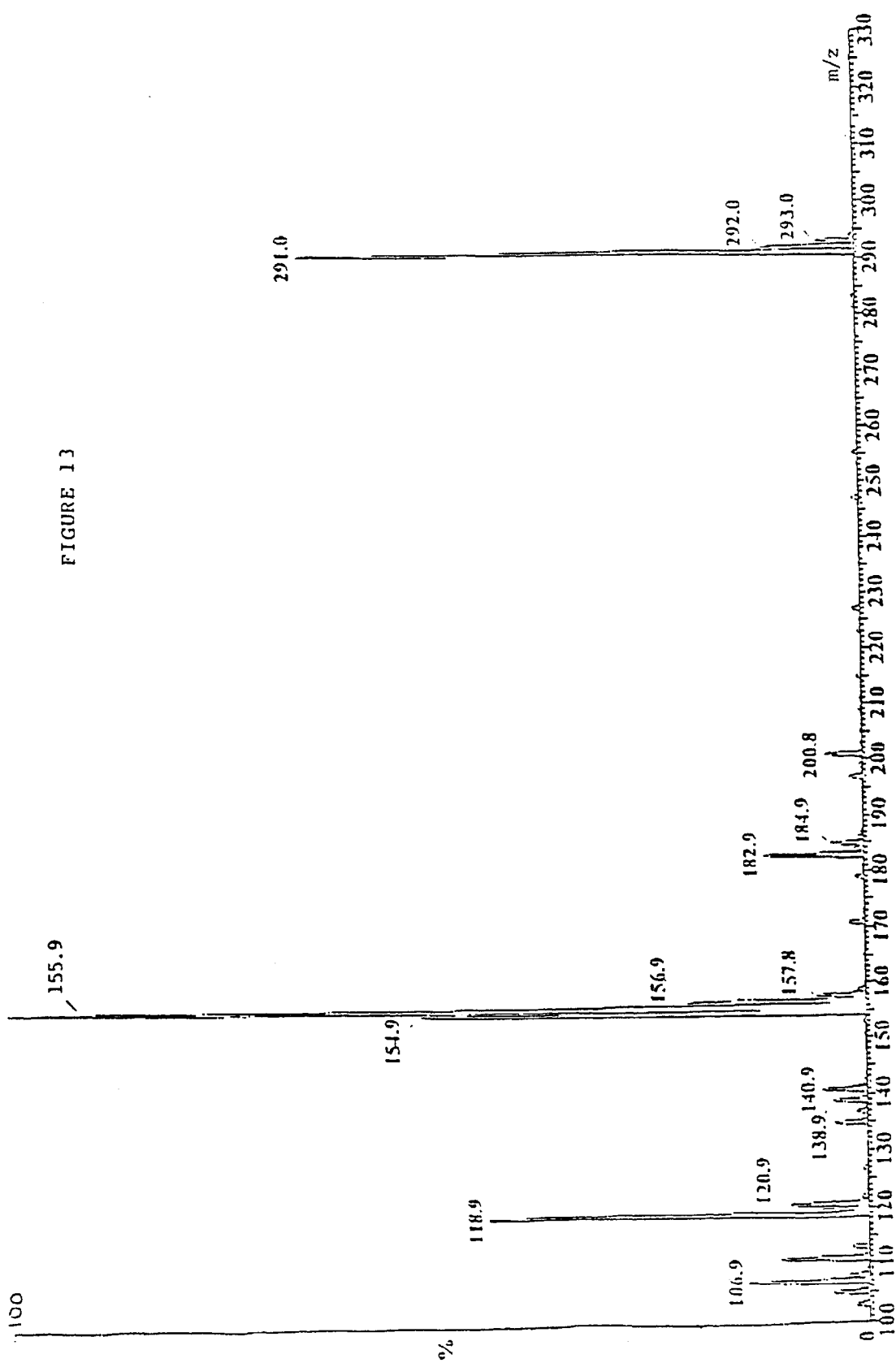
FIG. 13 shows a further mass spectrum of model compound AG/1/75 in positive ion mode.

FIG. 13 shows a negative ion spectrum of AG/1/75 in the same solution as for the previous spectra but with a cone voltage of 75 V. This voltage is sufficient to cause significant fragmentation in the molecule generating a major negative fragment ion peak at m/z 156 daltons, corresponding to the cleavage at the position shown in the inset structure in FIG. 13.

Figure 14:
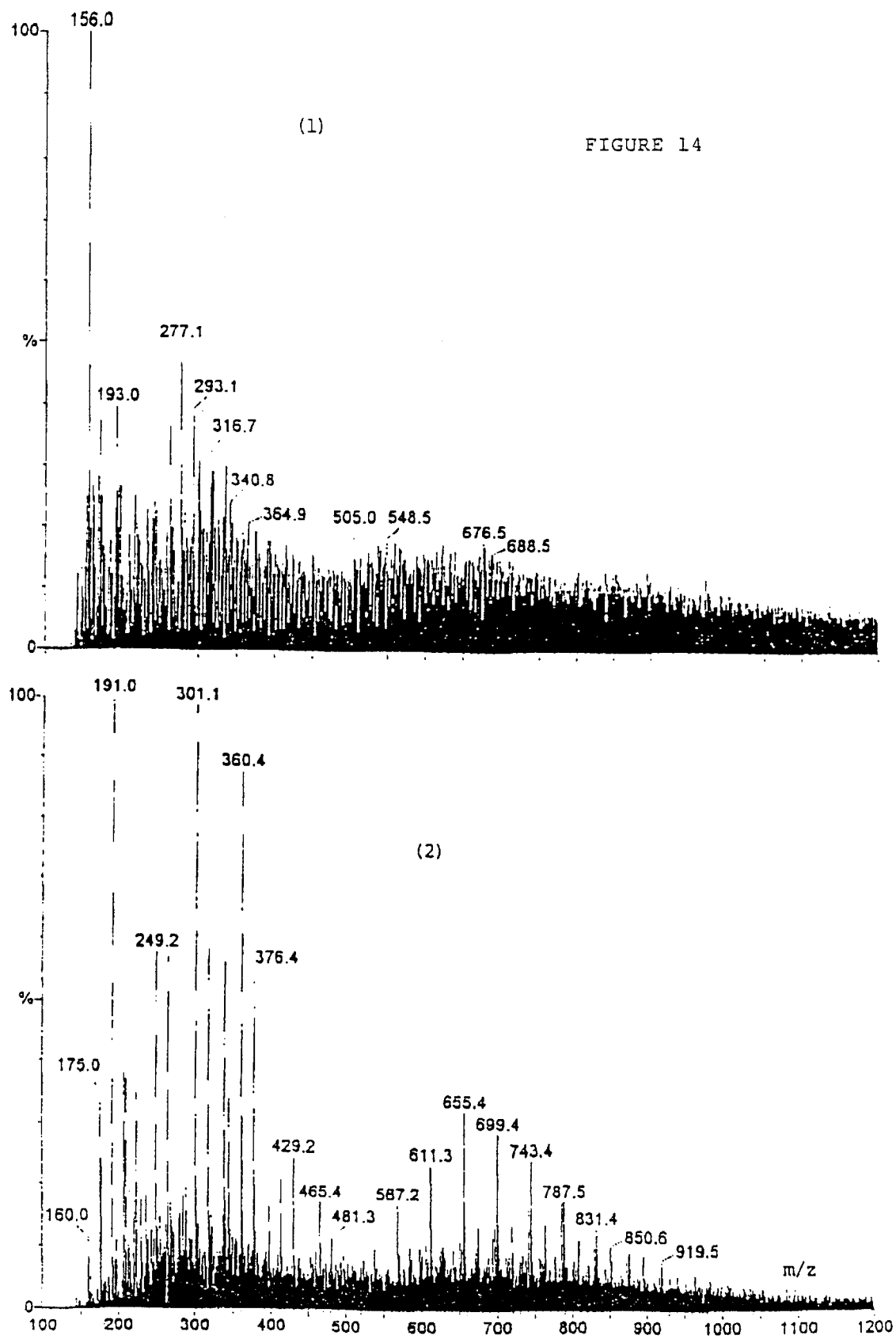
FIGS. 14 and 15 show mass spectra of a PCR product in various buffers in positive and negative modes.
Figure 15:
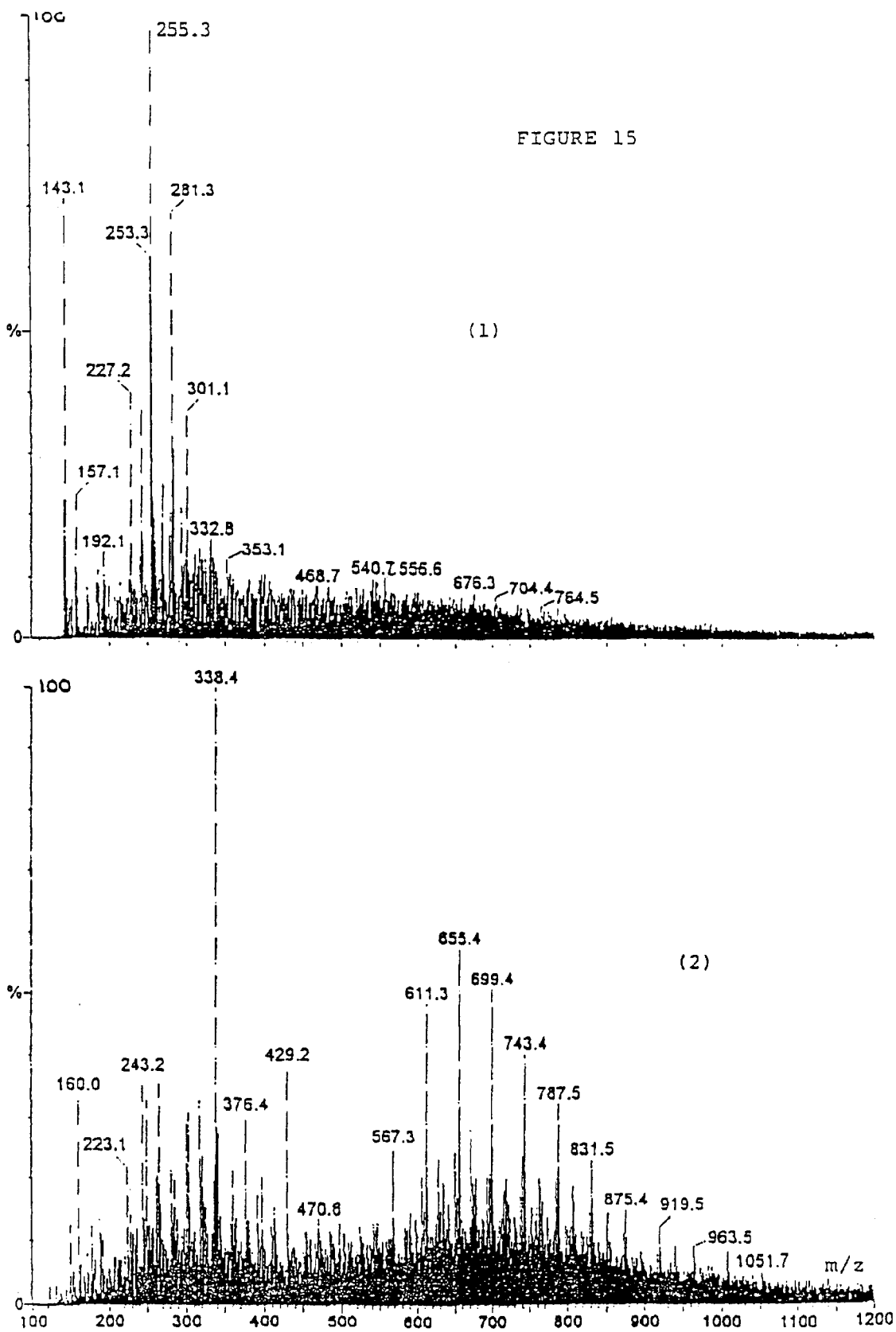
Figure 16:
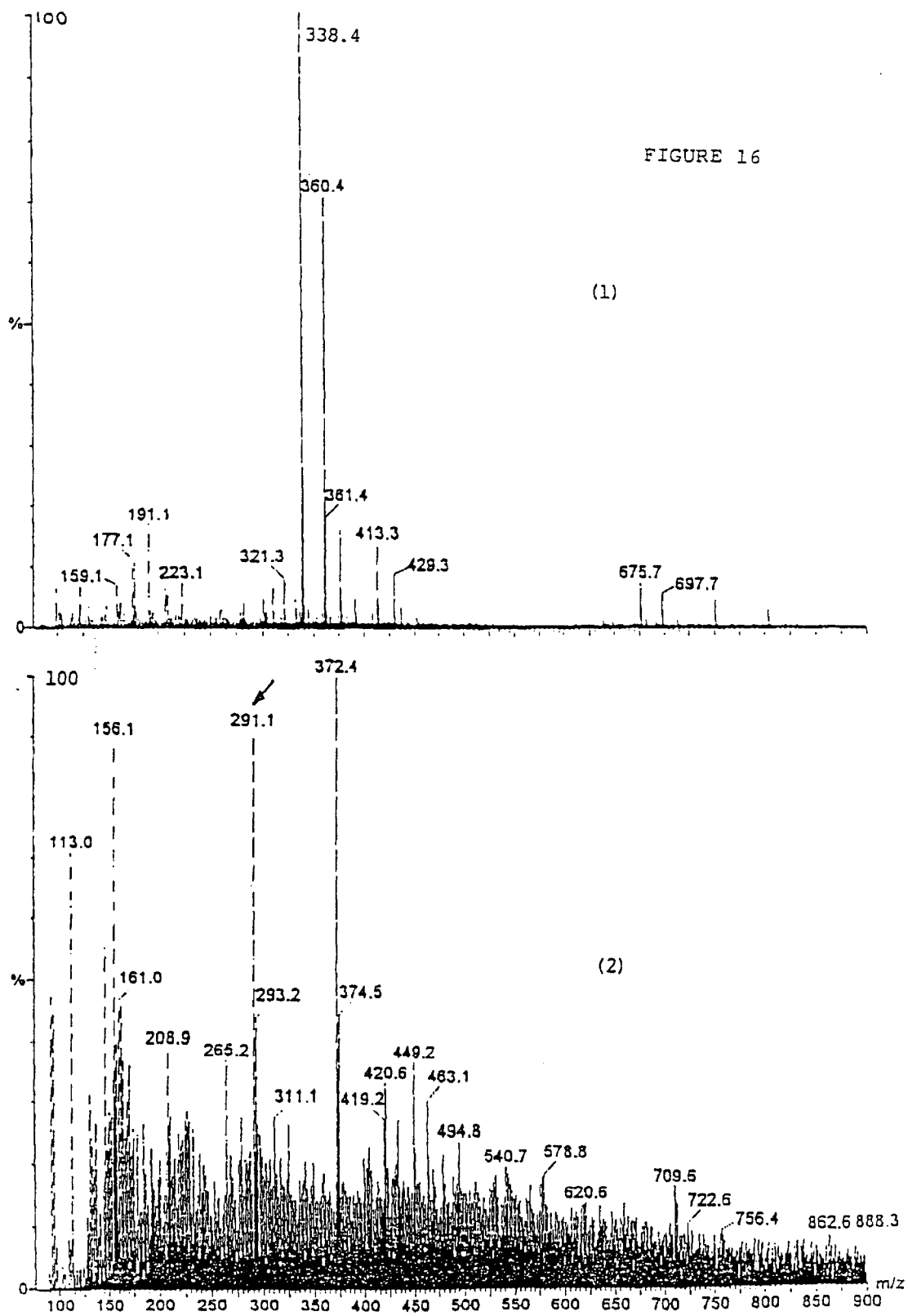
FIGS. 16 and 17 show mass spectra of the PCR product with AG/1/75 in negative and positive ion modes.
Figure 17:
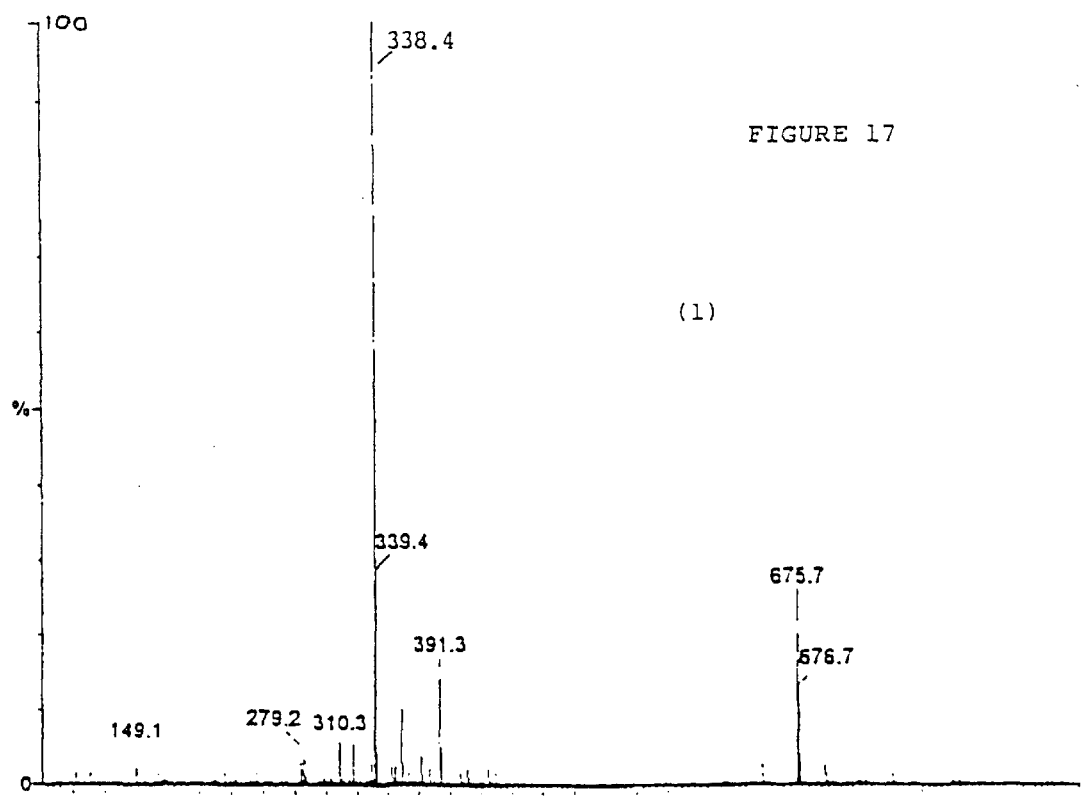
Figure 17:
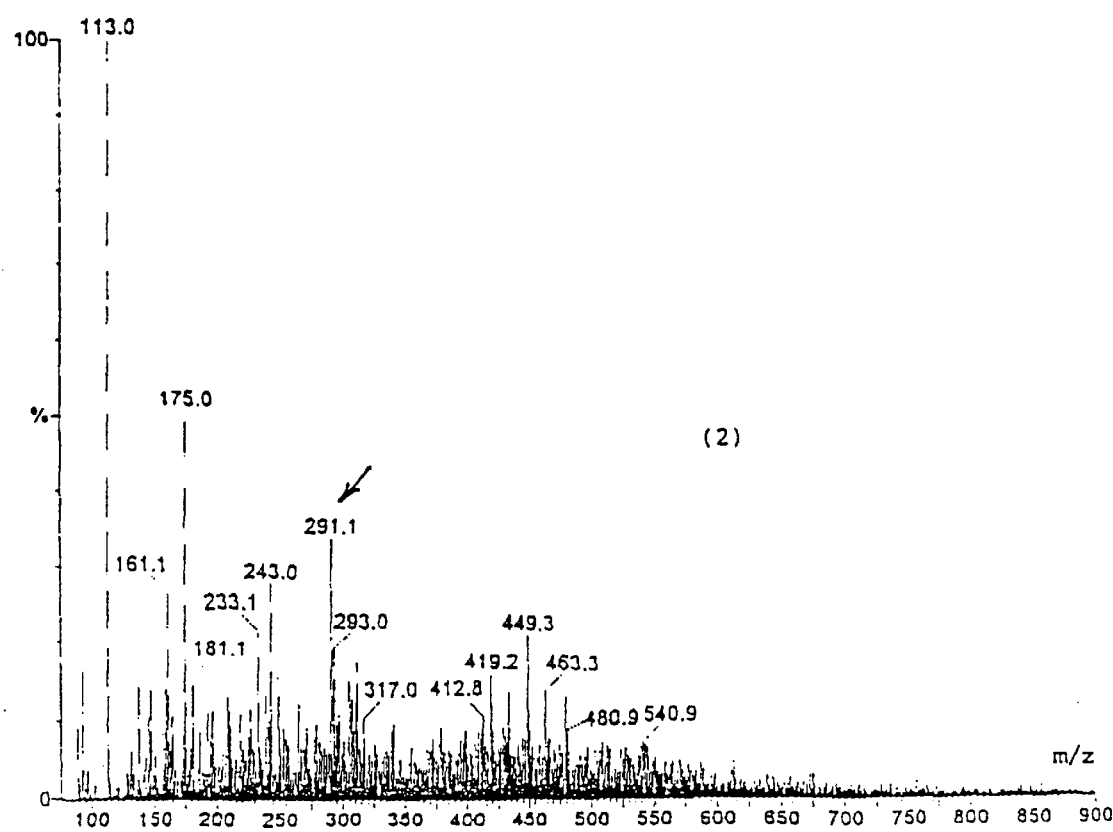
Figure 18:
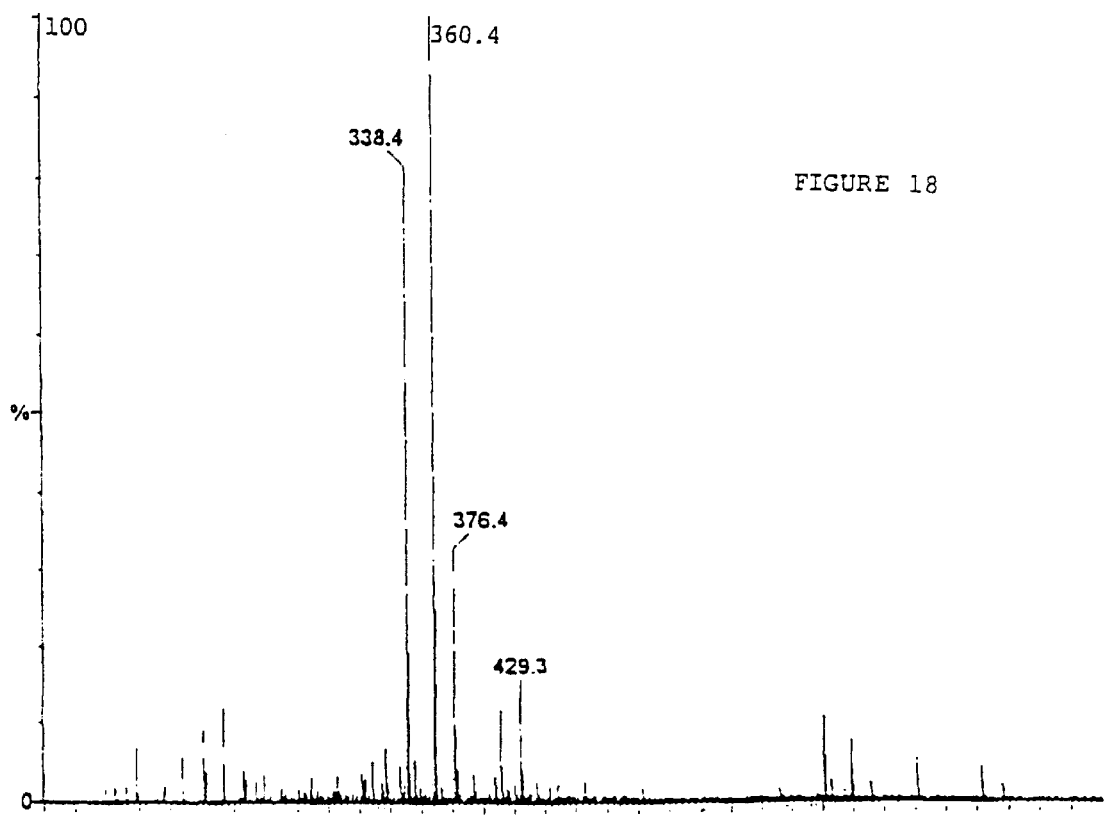
FIGS. 18 and 19 show mass spectra of the PCR product with AG/1/75 after signal processing.
Figure 18:
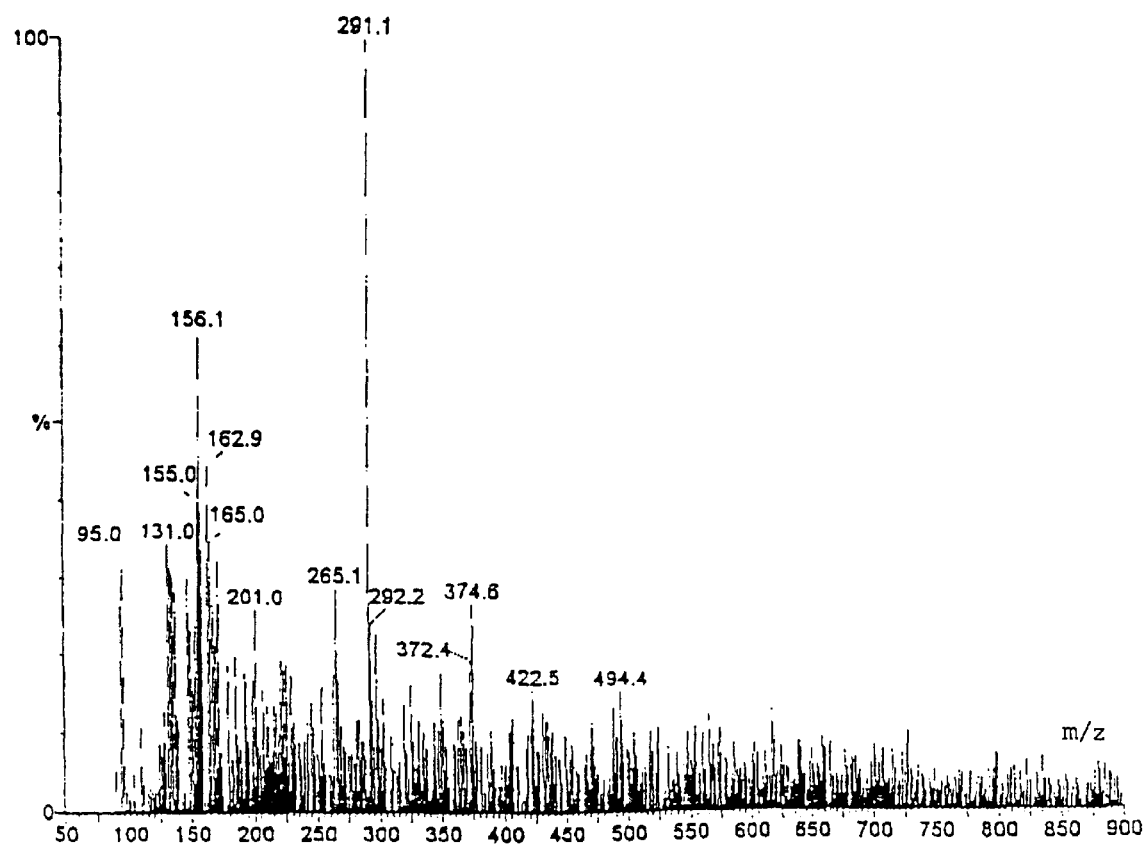
Figure 19:
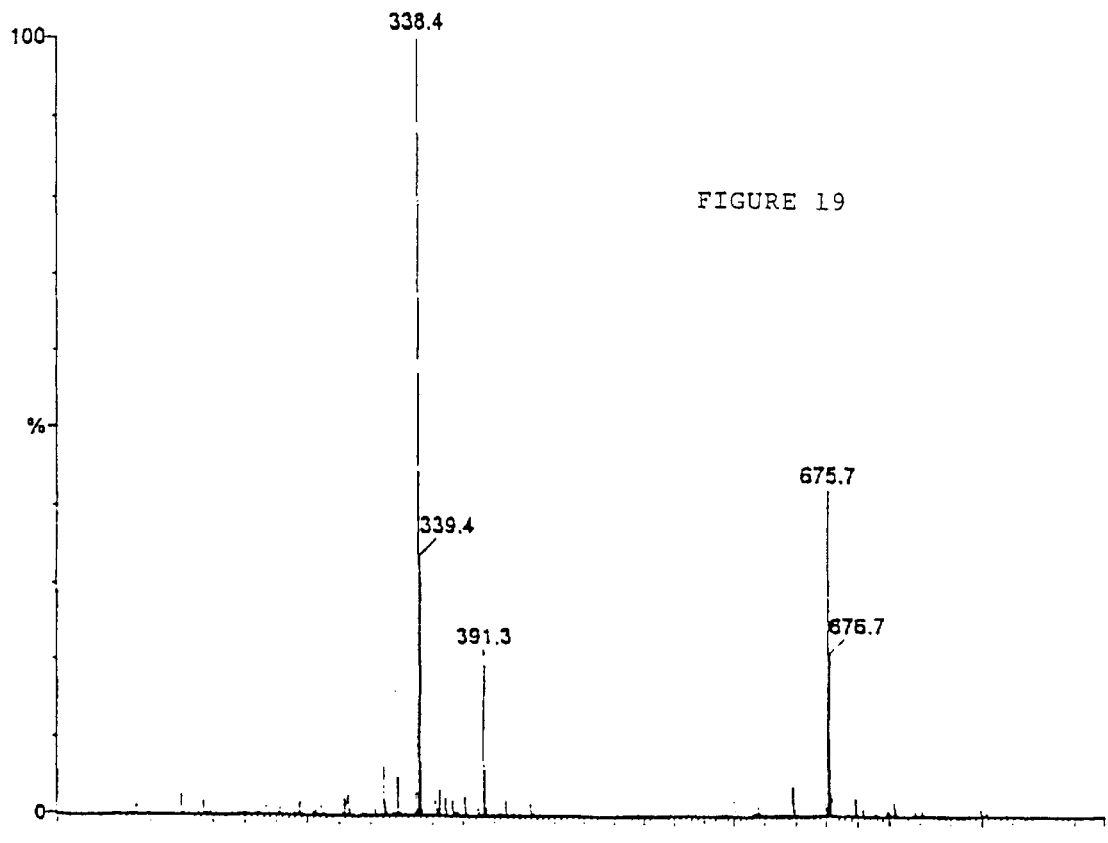
Figure 19:
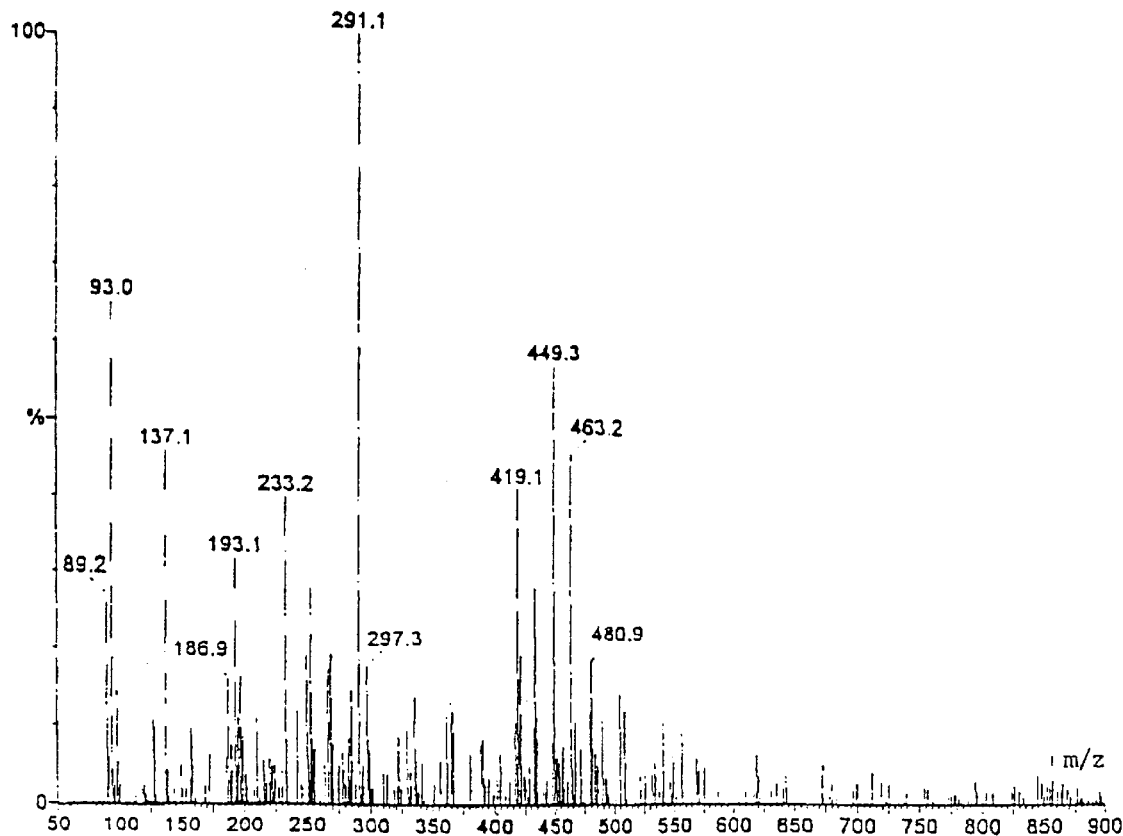

FIGS. 14 and 15l show mass spectra of an 'unconditioned' PCR product in various buffers, in positive and negative modes. The PCR product was 'unconditioned' in that no effort had been made to separate the DNA from the buffer and reaction material beyond what is normally done for gel electrophoresis. No attempt was made to exchange metal ion adducts for ammonium ions or to generate pure DNA as is usual practice for mass spectrometry purposes. FIGS. 16 and 17 show the same PCR product with AG/1/75 which can clearly be detected in the negative ion mode but not in the positive mode. FIGS. 18 and 19 show the same spectra after signal processing to subtract background noise and it is clear that AG/1/75 can be easily detected in the negative ion mode.

EXAMPLE 2

Synthesis of a Base, Mass-Labelled With an Aryl Ether

The following are protocols for the synthesis of a series of aryl ethers of thymidine nucleotides. The structures of these compounds are shown in FIGS. 24 and 25.

Figure 24:
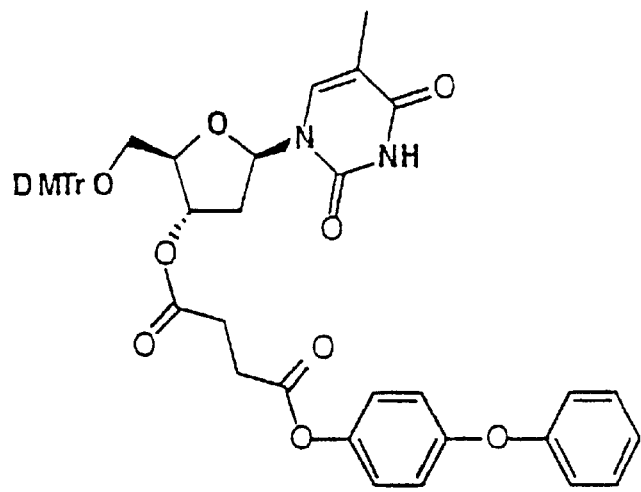
FIG. 24 shows mass labelled bases FT9 and FT17 according to the present invention.
Figure 24:
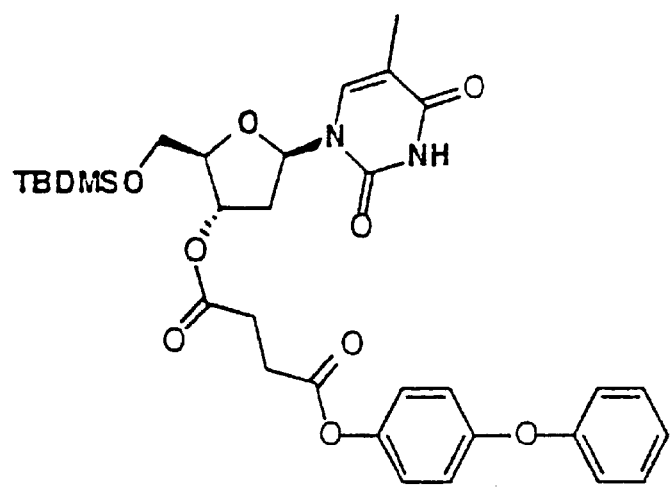
Figure 25:
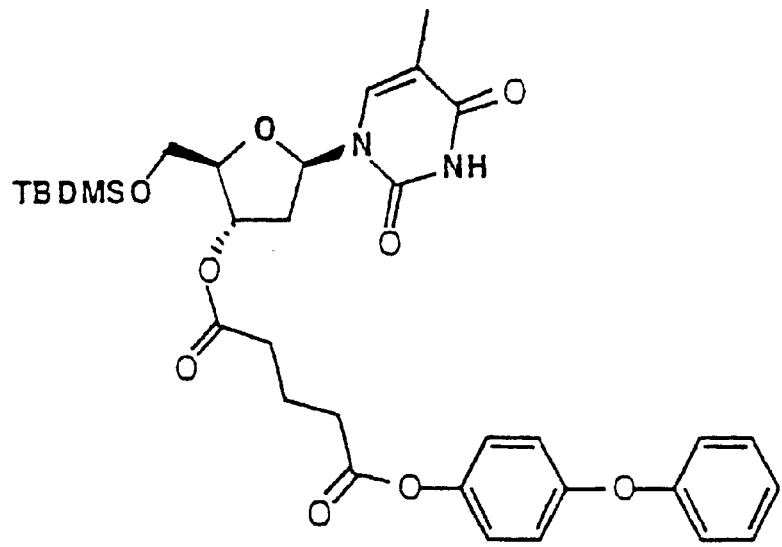
FIG. 25 shows mass labelled bases FT18 and FT23 according to the present invention.
Figure 25:
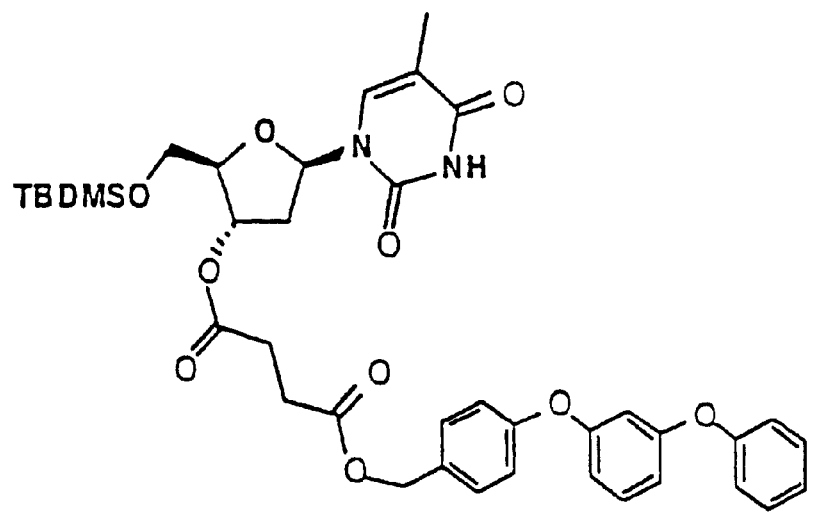

FT 9 (See FIG. 24)

A solution of 5' -O-(4,4'-dimethoxytrityl)-3'-succinoylthymidine (161 mg, 0.25 mmol) in dichloromethane (4 mL) was treated with N-methylmorpholine (27 µL, 0.25 mmol) and 2-chloro-4,6-dimethoxytriazine (44 mg, 0.25 mmol) and the whole was stirred for 1 h at room temperature. Then 4-phenoxyphenol (51 mg, 0.27 mmol) was added and stirring was continued for 5 days. The reaction mixture was diluted with dichloromethane and washed with an aqueous solution of citric acid (10% w/v) and twice with water. The organic phase was dried (Na₂SO₄) and the solvent was remove4 under reduced pressure. The residue was purified by flash chromatography using ethyl acetate/n-hexane (2:1) containing 1% of triethyl amine as eluate to give 86 mg (42% yield) of FT 9 as a colourless foam. $^1$H NMR (CDCl₃): δ 1.39 (3 H, m); 2.46 (2 H, m); 2.75 (2 H, m); 2.86 (2 H, m) 3.48 (2 H, m); 3.78 (6 H, s); 4.14 (1 H, m); 5.52 (1 H, m); 6.44 (1 H, m); 6.75–7.45 (22 H, m); 7.60 (1 H, d). MS (FAB), m/z 812 (M⁺). Calcd. for $C_{47}H_{44}N_2O_{11}$: C 69.44; H 5.46; N 3.46% Found: C 69.66; H 5.53; N 3.24%.

FT 17 (see FIG. 24)

A solution of 5'-O-(tert-butyldimethylsilyl)-3'-succinoylthymidine (288 mg, 0.5 mmol) in dichloromethane (3 mL) was treated with three drops of pyridine and then dropwise with a solution of oxalyl chloride (2M; 0.3 mL, 0.6 mmol) in dichloromethane. The reaction mixture was stirred for 90 min at room temp. The solution of the so-formed acid chloride was added dropwise to an ice-cold solution of 4-phenoxyphenol (110 mg, 0.59 mmol) and pyridine (0.3 mL) in dichloromethane (3 mL). After 30 min a further portion of 4-phenoxyphenol (35 mg, 0.19 mmol) in dichloromethane (0.7 mL) were added and stirring was continued for 4 h. The reaction mixture was diluted with dichloromethane and washed with an aqueous solution of NaHCO₃ (5% w/v) and twice with water. The organic phase was dried with (Na₂SO₄) and the solvent was removed under reduced pressure. The residue was purified by flash chromatography using ethyl acetate/n-hexane (1:1) as eluant to give 145 mg (47% yield) of FT 17 as a colourless foam. $^1$H NMR (CDCl₃): δ0.12 (6H); 0.92 (9H); 1.92 (3H, s); 2.12 (1H, m); 2.40 (1H, m); 2.77 (2H, m); 2.89 (2H); 3.90 (2H, d); 4.11 (1H, d); 5.30 (1H, d); 6.36 (1H, dd) 7.00–7.27 (9H, m); 7.54 (1H, d); 8.26 (1H, br s). MS (FAB) m/z 625 [M+H]⁺. Calcd. for $C_{32}H_{40}N_2O_9Si$: C 61.52; H 6.45; N 4.48% Found: C 61.60; H 6.45; N 4.45.

FT 18/1 (see FIG. 25)

A solution of 4-phenoxyphenyl glutarate (180 mg, 0.6 mmol) in dichloromethane (3 mL) was treated with three drops of pyridine and then dropwise with a solution of oxalyl chloride (2M; 0.35 mL, 0.7 mmol) in dichloromethane. The reaction mixture was stirred for 90 min at room temperature. The solution of the so-formed acid chloride was added dropwise to an ice-cold solution of 5'-O-(tert-butyldimethylsilyl)thymidine (228 mg, 0.5 mmol) and pyridine (0.3 mL) in dichloromethane (3 mL). Stirring was continued for 5 h at room temperature. The reaction mixture was diluted with dichloromethane and washed with aqueous NaHCO₃ (5% w/v) and twice with water. The organic phase was dried (Na₂SO₄) and the solvent was removed under reduced pressure. The residue was purified by flash chromatography using ethyl acetate/n-hexane (1:1) as eluant to give 111 mg (35% yield) of FT 18/1 as a colurless oil. $^1$H NMR (CDCl₃): δ 0.12 (6H); 0.92 (9H, s); 1.92 (3H, s); 2.02–2.30 (3H, m); 2.35–2.75 (5H, m); 3.92 (2H, d); 4.10 (1H, d); 5.29 (1H, d); 6.36 (1H, dd); 6.97–7.37 (9H, m); 7.54 (1H, d); 8.65 (1H, br s). MS (FAB), m/z 639 [M+H]⁺. Calcd. for $C_{33}H_{42}N_2O_9Si(H_2O)$: C 60.35; H 6.75; N 4.26%, Found: C 60.57; H 6.60; N 4.18%.

F23 (see FIG. 25)

A solution of 5'-O-(tert-butyldimethylsilyl)-3'-succinoylthymidine (288 mg, 0.5 mmol) in dichloromethane (3 mL) was treated with three drops of pyridine and then dropwise with of a solution of oxalyl chloride (2M; 0.3 mL, 0.6 mmol) in dichloromethane. The reaction mixture was stirred for 90 min at room temperature. The solution of the so-formed acid chloride was added dropwise to an ice-cold solution of of (4'-phenoxy)-4-phenoxybenzyl alcohol (146 mg, 0.5 mmol) and pyridine (0.3 mL) in dichloromethane (3 mL). Stirring was continued for 4 h at room temperature. The reaction mixture was diluted with ethyl acetate and washed with aqueous NaHCO₃ (5% w/v) and twice with water. The organic phase was dried with (Na₂SO₄) and the solvent was removed under reduced pressure. The residue was purified by flash chromatography using ethyl acetate/n-hexane (1:1) to give 73 mg (20% yield) of FT 23. $^1$H NMR (CDCl₃): δ 0.13 (6H, s); 0.92 (9H, s); 1.92 (3H, s); 2.11 (1H, m); 2.39 (1H, m); 2.68 (4H, s); 3.90 (2H, d); 4.06 (1H; d); 5.11 (2H, s); 5.27 (1H, d); 6.34 (1H; m); 6.95–7.37 (13H, m); 7.35 (1H, d); 8.27 (1H, br s). MS (FAB) m/z 731 [M+H]⁺. Calcd.

for $C_{39}H_{46}N_2O_{10}Si$: C 64.08; H 6.34; N 3.85%, Found: C 64.32; H 6.38; N 3.79%.

Mass Spectrometry of Mass-Labelled Base FT23

Figure 20:
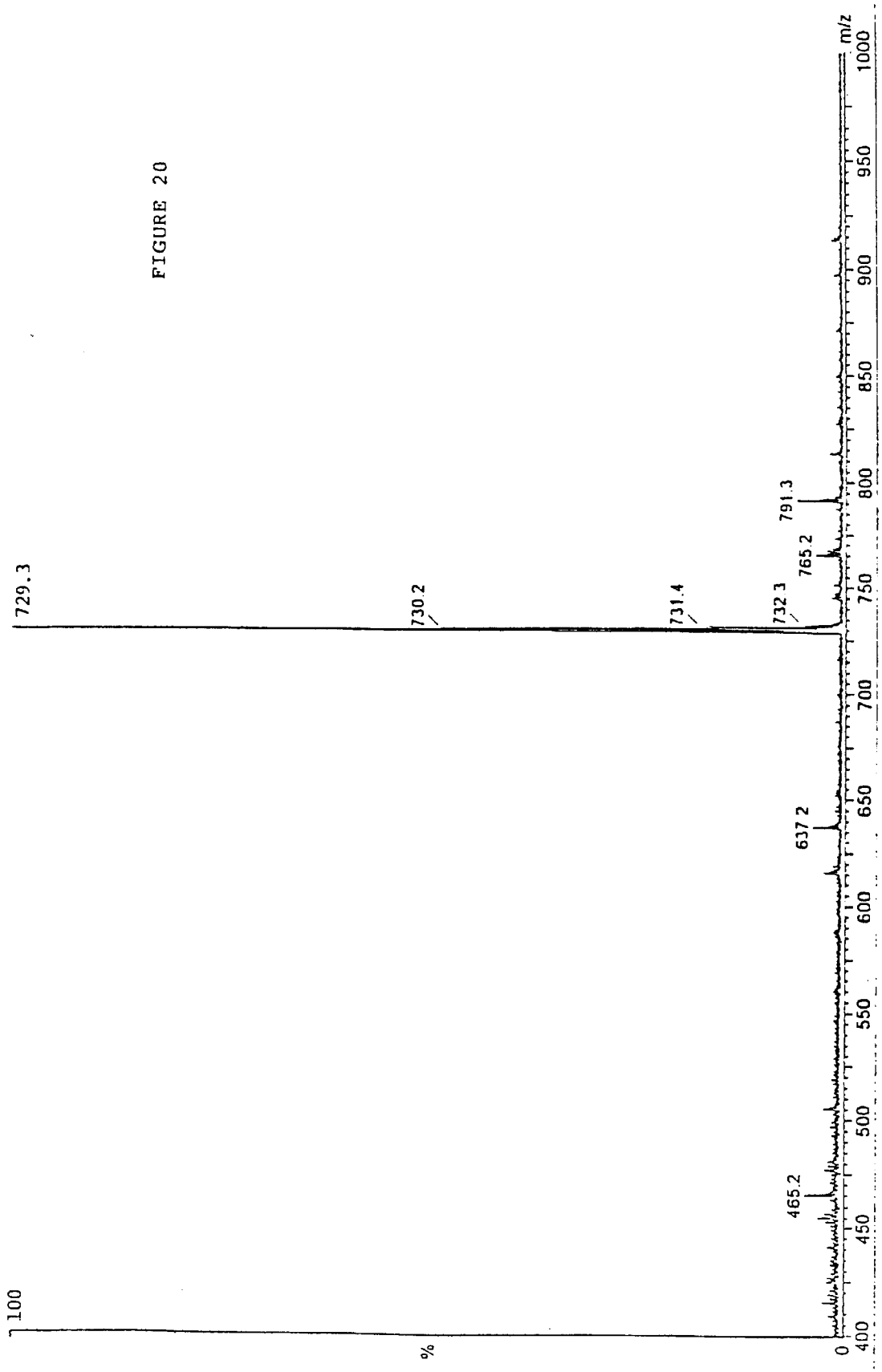
FIGS. 20 and 21 show mass spectra of mass labelled base FT23 in negative and positive ion modes.
Figure 21:
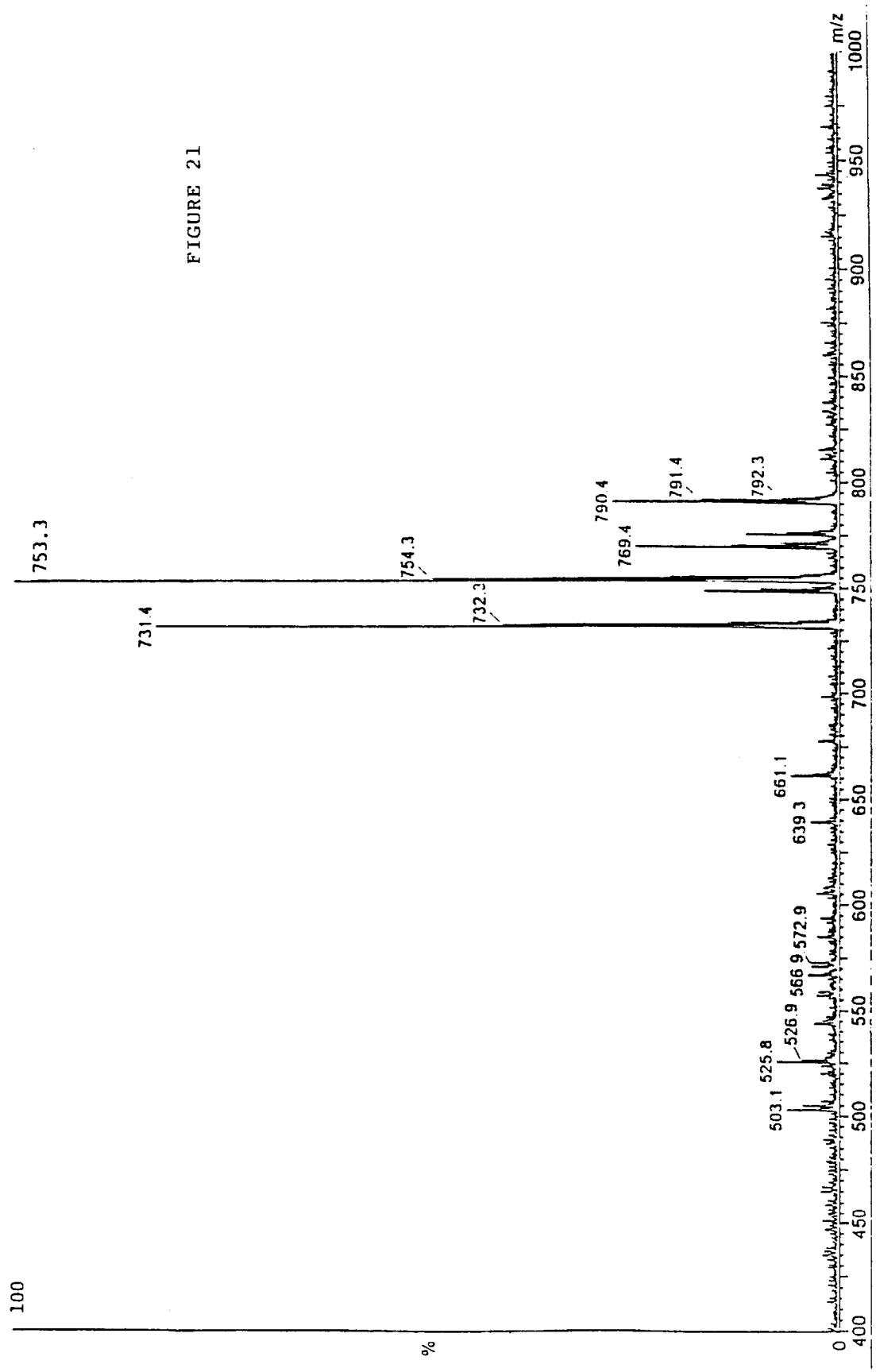

Mass spectrometric studies were performed on FT23 as a model for the behaviour of a mass-labelled base in the presence and absence of an oligonucleotide background. The results of these studies are presented in FIGS. 20 to 23. Each Figure shows a mass spectrum generated by using an electrospray ion source, with a cone voltage of 45 v, in a Platform-LC quadrupole scanning mass spectrometer (Micromass UK). In each case, FT23 was present at 4 pmol/µl. FIG. 20 shows the mass spectrum in negative ion mode with a prominent peak at 729.3 corresponding to the [M–H]⁻ ion. FIG. 21 shows the corresponding mass spectrum in positive ion mode with a number of prominent peaks.

Figure 22:
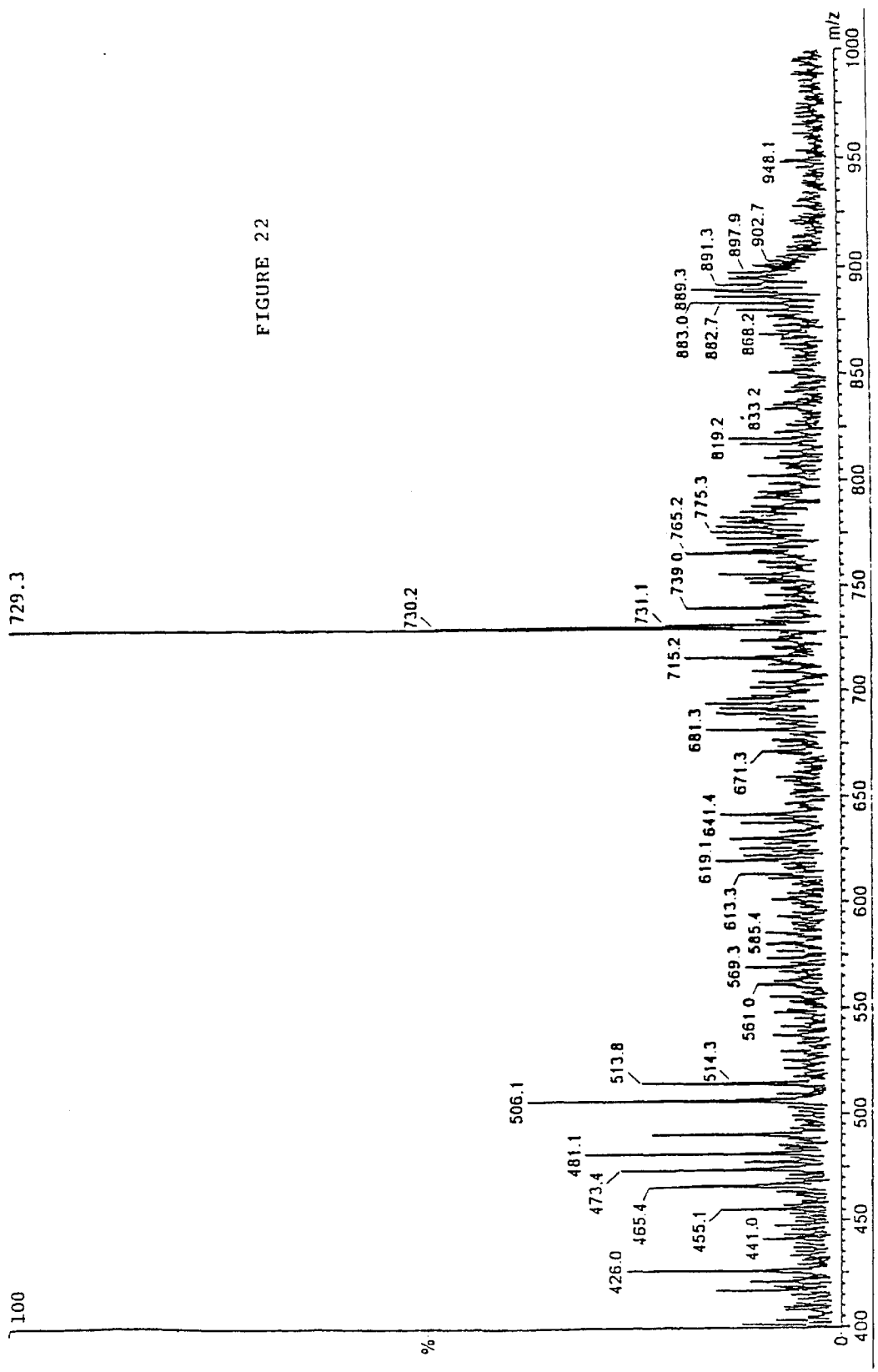
FIGS. 22 and 23 show mass spectra in negative and positive ion modes of FT23 with oligonucleotide background.
Figure 23:
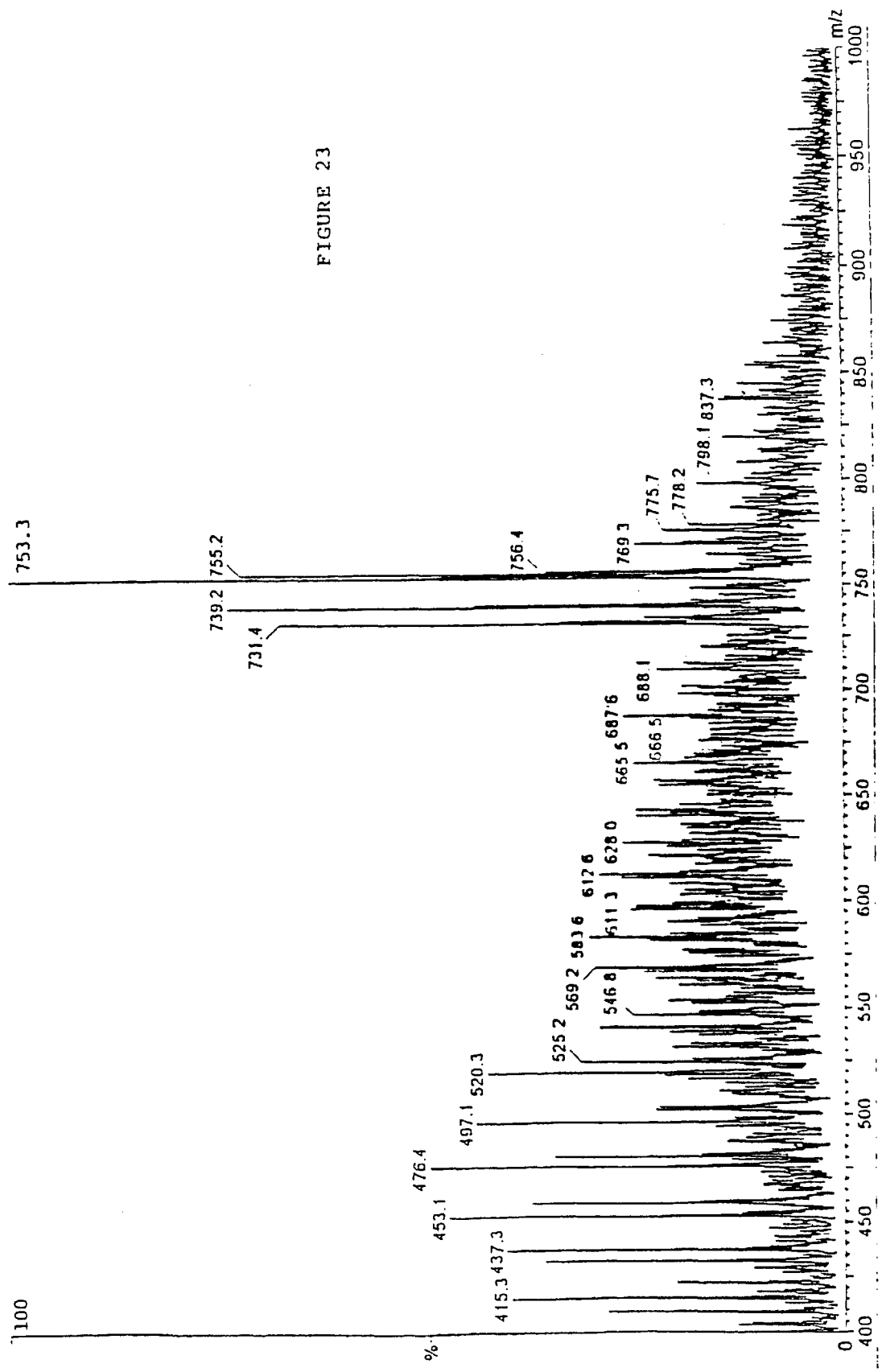

FIGS. 22 and 23 show respectively negative ion and positive ion mode mass spectra generated under the same conditions as those shown in FIGS. 20 and 21 with the exception that an oligonucleotide sample of approximate molecular weight 3000 is additionally present in each case at 4 pmol/µl. Once again, in negative ion mode (FIG. 22) a clear peak is discernible at 729.3. In positive ion mode (FIG. 23) a number of peaks is again detected.

These results indicate that the mass-labelled base FT23 is readily detectable in negative ion mode mass spectrometry even in the presence of equimolar (contaminating) oligonucleotide.

References

1. R. A. W. Johnstone and M. E. Rose, "Mass Spectrometry for chemists and biochemists" 2nd edition, Cambridge University Press, 1996
2. G. Jung and A. G. Beck-Sickinger, Angew. Chem. Int. Ed. Engl. 31, 367–383
3. S. Brenner and R. A. Lerner, "Encoded combinatorial chemistry", Proc. Natl. Acad. Sci. USA 89, 5381–5383
4. M. J. Bishop and C. J. Rawlings, editors, 'Nucleic Acid and Protein Sequence Analysis: A Practical Approach', IRL Press, Oxford, 1991
5. P. H. Nestler, P. A. Bartlett and W. C. Still, "A general method for molecular tagging of encoded combinatorial chemistry libraries", J. Org. Chem. 59, 4723–4724, 1994
6. Z-J. Ni et al, "Versatile approach to encoding combinatorial organic syntheses using chemically robust secondary amine tags", J. Med. Chem. 39, 1601–1608, 1996
7. H. M. Geysen et al, "Isotope or mass encoding of combinatorial libraries", Chemistry and Biology 3, 679–688, August 1996
8. British Patent Application No. 9618544.2
9. A. C. Pease et al. Proc. Natl. Acad. Sci. USA. 91, 5022–5026, 1994
10. U. Maskos and E. M. Southern, Nucleic Acids Research 21, 2269–2270, 1993
11. E. M. Southern et al, Nucleic Acids Research 22, 1368–1373, 1994
12. PCT/GB97/02403
13. British Patent Application No. 9620769.1
14. PCT/GB97/02722
15. WO97/27325
16. WO97/27327
17. WO97/27331
18. Lloyd-Williams et al., Tetrahedron 49: 11065–11133, 1993
19. J. F. Milligan, M. D. Matteucci, J. C. Martin, J. Med. Chem. 36(14), 1923–1937,1993
20. C. J. Guinosso, G. D. Hoke, S. M. Freier, J. F. Martin, D. J. Ecker, C. K. Mirabelle, S. T. Crooke, P. D. Cook, Nucleosides Nucleotides 10, 259–262, 1991
21. M. Carmo-Fonseca, R. Pepperkok, B. S. Sproat, W. Ansorge, M. S. Swanson, A. I. Lamond, EMBO J. 7, 1863–1873, 1991
22. (8) P. E. Nielsen, Annu. Rev. Biophys. Biomol. Struct. 24, 167–183, 1995
23. Zhen Guo et al., Nature Biotechnology 15, 331–335, April 1997
24. Wetmur, Critical Reviews in Biochemistry and Molecular Biology, 26, 227–259, 1991
25. Sambrook et al, 'Molecular Cloning: A Laboratory Manual, 2nd Edition', Cold Spring Harbour Laboratory, New York, 1989
26. Hames, B. D., Higgins, S. J., 'Nucleic Acid Hybridisation: A Practical Approach', IRL Press, Oxford, 1988
27. Gait, M. J. editor, 'Oligonucleotide Synthesis: A Practical Approach', IRL Press, Oxford, 1990
28. Eckstein, editor, 'Oligonucleotides and Analogues: A Practical Approach', IRL Press, Oxford, 1991
29. Vogel's "Textbook of Organic Chemistry" 4th Edition, Revised by B. S. Furniss, A. J. Hannaford, V. Rogers, P. W. G. Smith & A. R. Tatchell, Longman, 1978
30. Advanced Organic Chemistry by J. March
31. E. Atherton and R. C. Sheppard, editors, 'Solid Phase Peptide Synthesis: A Practical Approach', IRL Press, Oxford Key to Figures Key to FIG. 1

Step 1: Generate cDNA captured on solid phase support, e.g. using biotinylated poly-T primer Step 2: Treat retained poly-A carrying cDNAs with 'reference enzyme' and wash away loose fragments Step 3: Add adaptor with sticky-end complementary to 'reference enzyme' sticky-end and carrying a binding site for 'sampling enzyme'. Adaptor can also carry primer sequence to permit linear amplification of template Step 4: Treat adaptored cDNAs with 'sampling endcnuclease' and wash away loose fragments Step 5: Add adaptor with sticky-end complementary to 'reference enzyme' sticky-end and carrying a binding set for the 'sampling enzyme'. The adaptor should also carry a mass-label with a photocleavable linker Step 6: Add 'sampling enzyme'

Figure 2A:
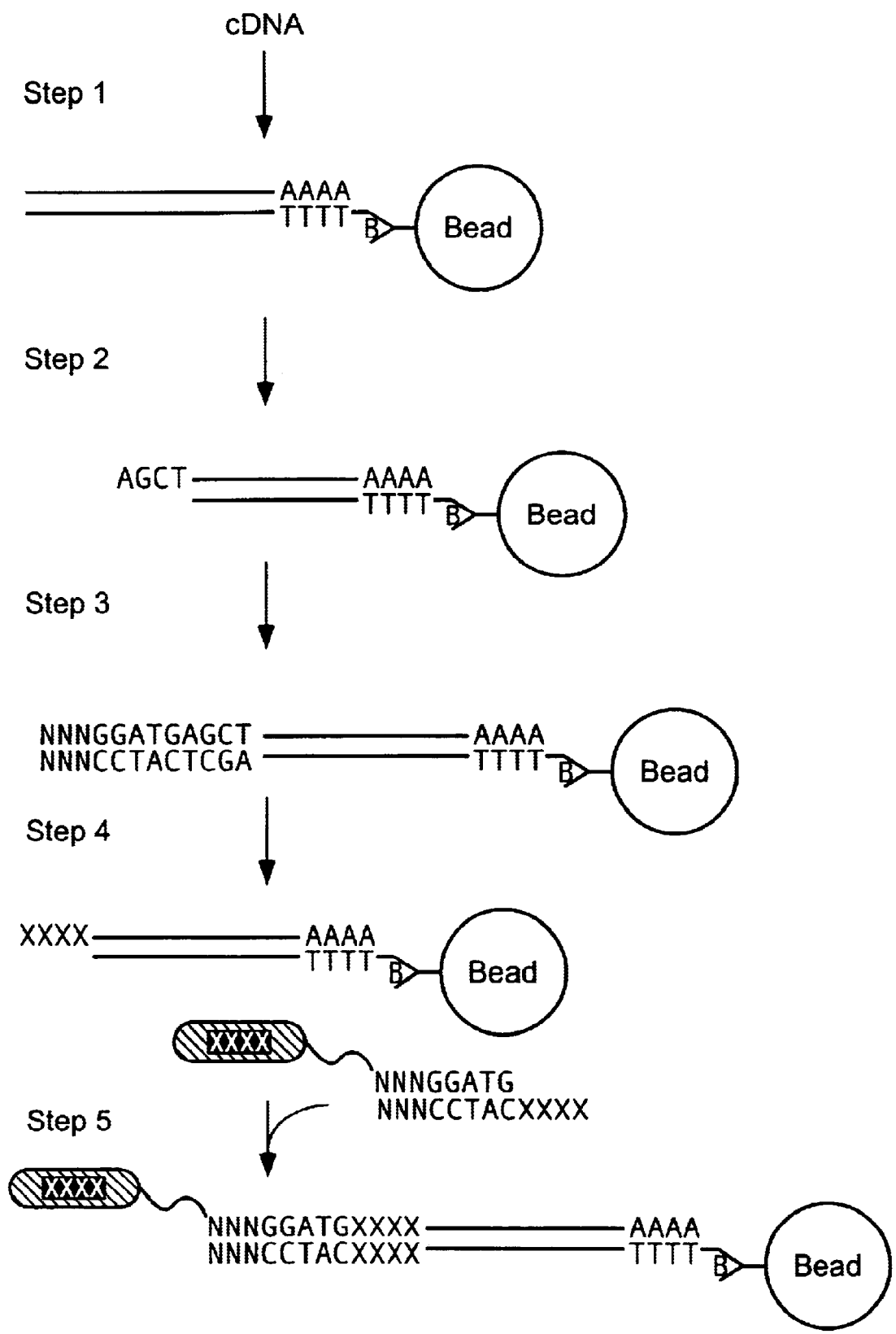
FIGS. 2a and 2b show use of mass labelled hybridisation probes according to the present invention in a further method of gene expression profiling.

Step 7: Remove liquid phase into which signature fragments have been released and ligate onto oligonucleotide array carrying all of the possible 256 4-mers at discrete locations on a glass chip Step 8: Embed ligated signatures in MALDI MATRIX. Transfer chip with ligated signatures to a MALDI mass spectrometer Step 9: Scan chip with a laser to cleave mass labels from signatures in one field on the chip. Scan the same region with a UV laser at a second frequency to ionise mass labels that have been cleaved for analysis by mass spectrometry Key to FIG. 2a Step 1: Pass through matrix with biotin-labelled poly-T bound to avidin coated beads Step 2: Treat retained poly-A carrying cDNAs with 'reference endonuclease' and wash away loose fragments Step 3: Add adaptor with sticky-end complementary to 'reference enzyme' sticky-end and carrying a binding site for 'sampling endonuclease'

Figure 2B:
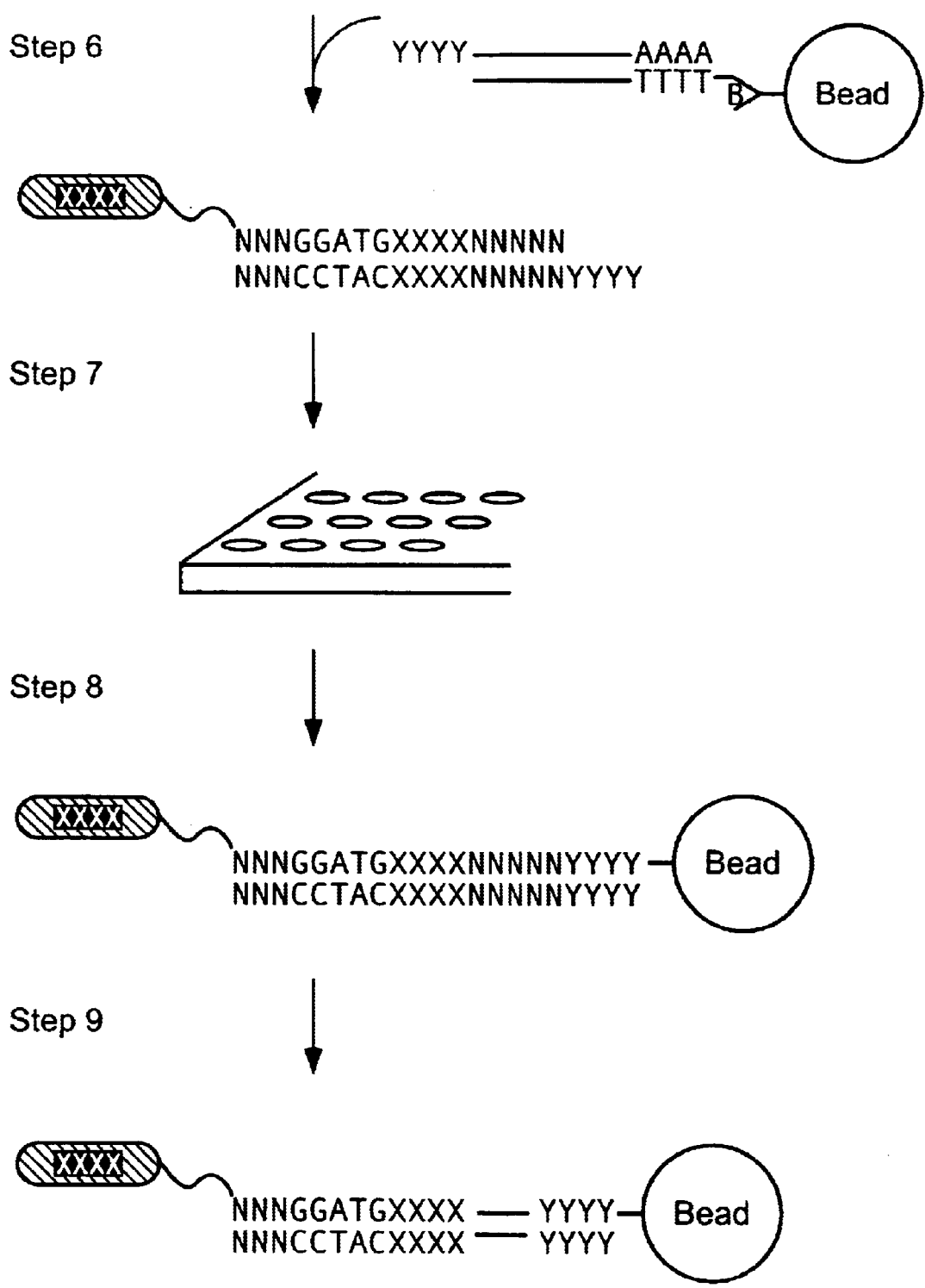
Figure 3A:
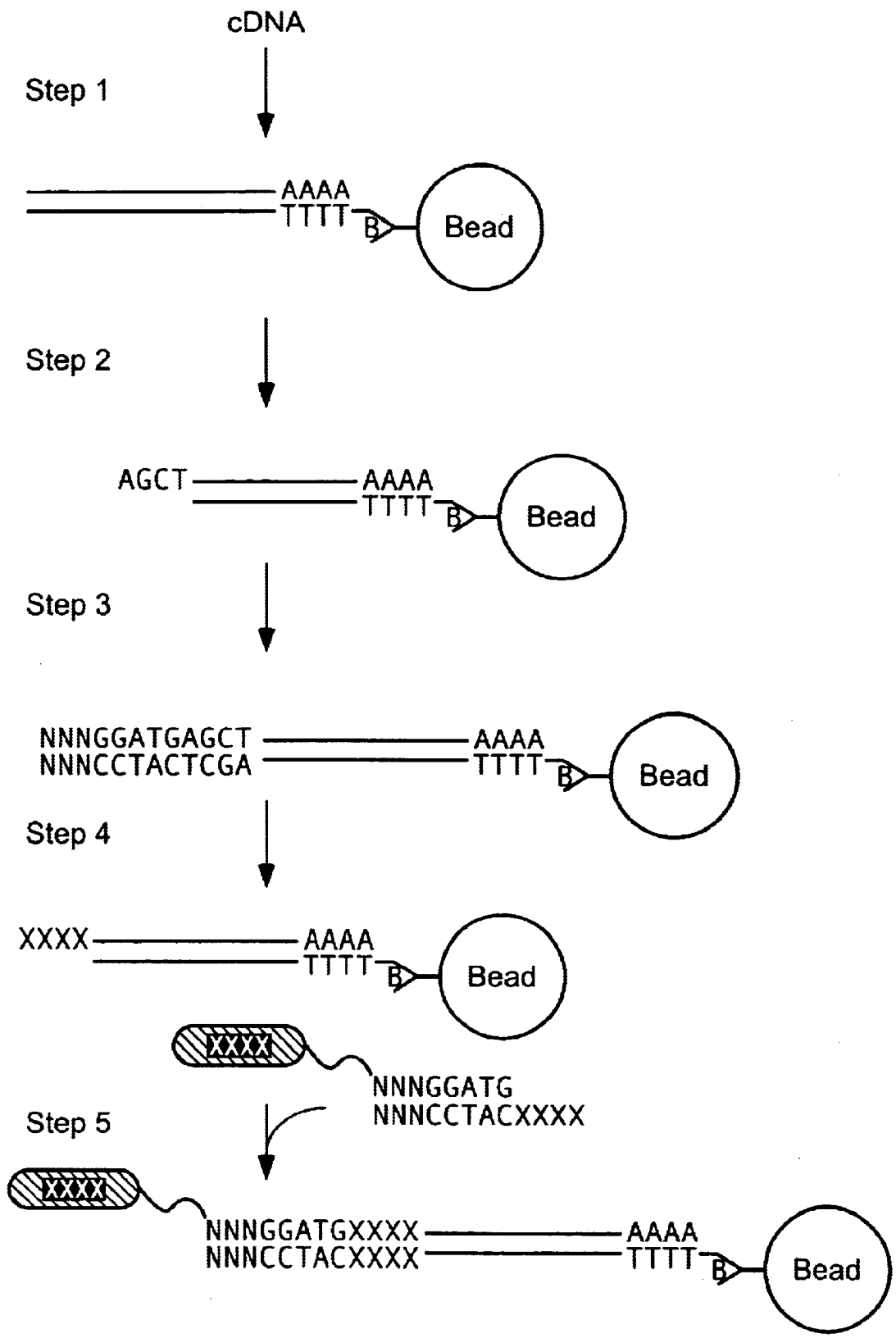
FIGS. 3a and 3b show use of mass labelled hybridisation probes according to the present invention in a further method of gene expression profiling.
Figure 3B:
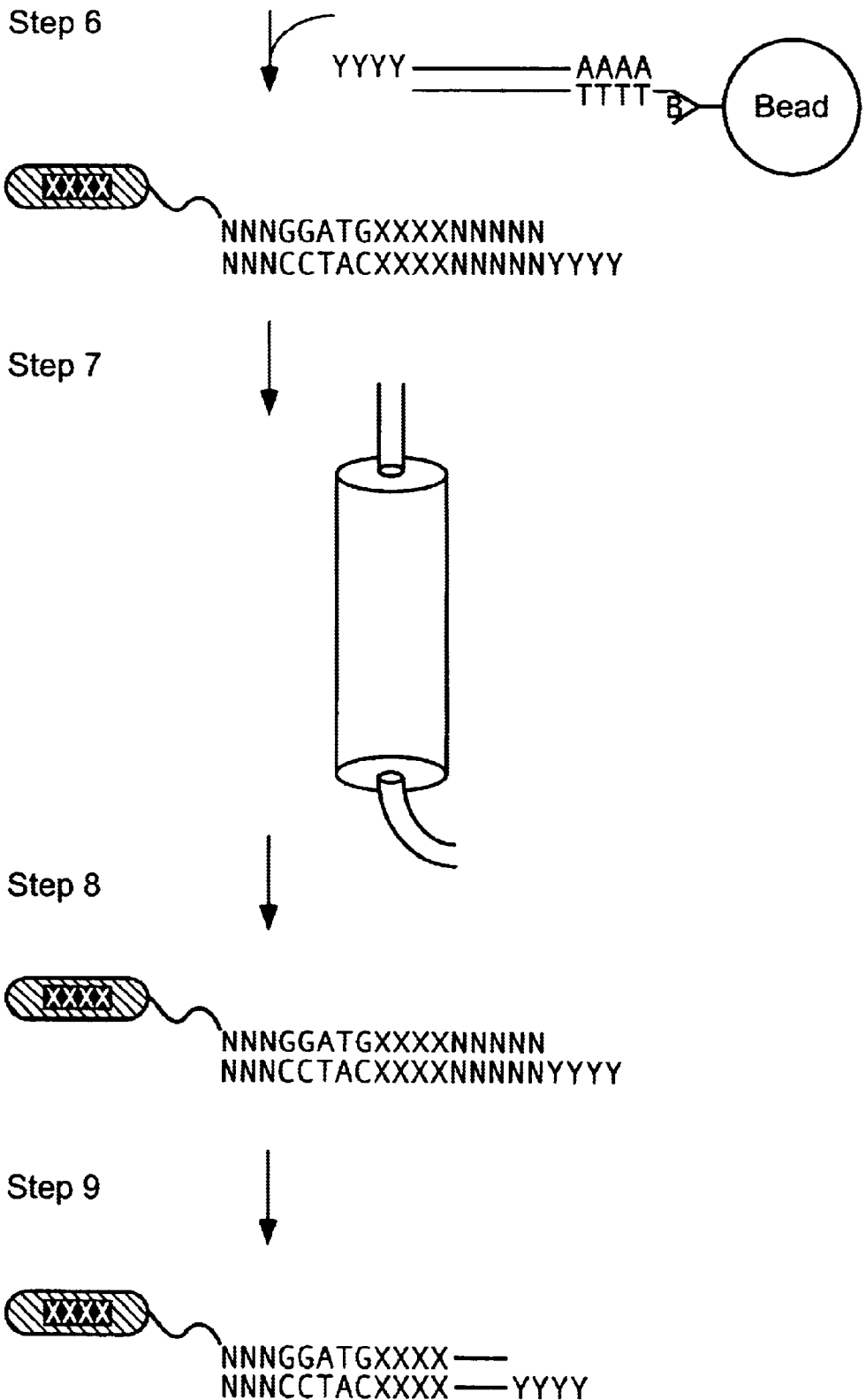
Figure 4:
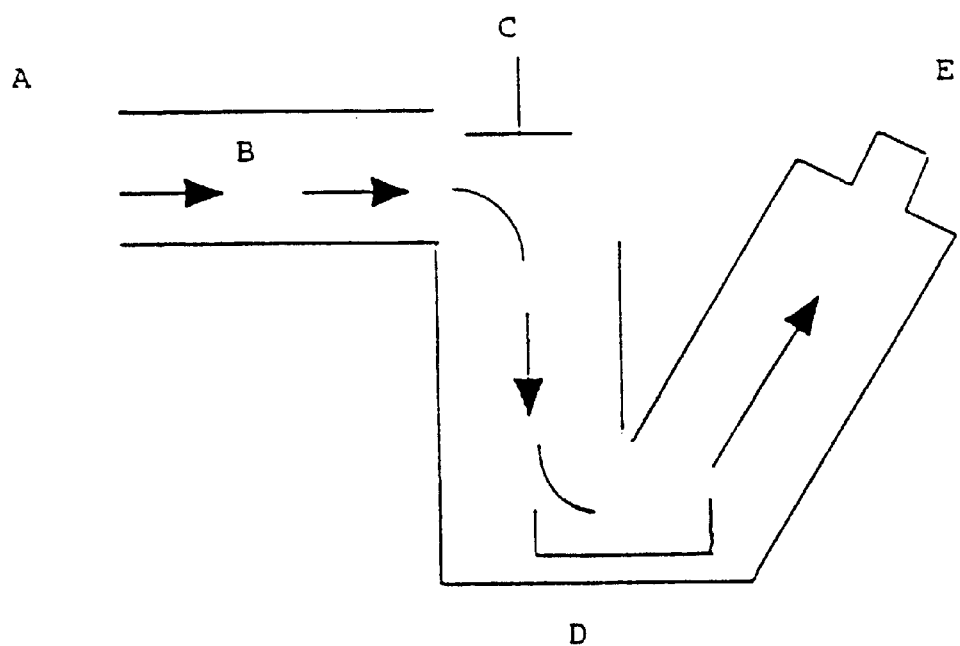
FIG. 4 shows a schematic diagram of an orthogonal time of flight mass spectrometer suitable for use in the present invention.

Step 4: Add 'sampling enzyme'
Step 5: Add adaptors with sticky-ends complementary to all possible 4 base sticky-ends and carrying a binding site for 'sampling endonuclease'. These adaptors will also carry a 'mass label' to identify the sequence of the ambiguous sticky-end that they identify
Key to FIG. 2b
Step 6: Add 'sampling enzyme'
Step 7: Remove liquid phase into which signature fragments have been released and divide into 256 wells
Step 8: Ligate signatures to beads in well. Each well would contain beads corresponding to one possible sticky-end. Wash away any unligated signatures in each well
Step 9: Cleave mass label from immobilised signature fragments, thus releasing it into liquid phase, and analyse by electrospray mass spectrometry
Key to FIG. 3a
Step 1: Pass through matrix with biotin-labelled poly-T bound to avidin coated beads
Step 2: Treat retained poly-A carrying cDNAs with 'reference endonuclease' and wash away loose fragments
Step 3: Add adaptor with sticky-end complementary to 'reference enzyme' sticky-end and carrying a binding site for 'sampling endonuclease'
Step 4: Add 'sampling enzyme'
Step 5: Add adaptors with sticky-ends complementary to all possible 4 base sticky-ends and carrying a binding site for 'sampling endonuclease'. These adaptors will also carry a 'mass label' to identify the sequence of the ambiguous sticky-end that they identify
Key to FIG. 3b
Step 6: Add 'sampling enzyme'
Step 7: Remove liquid phase into which signature fragments have been released and load into HPLC affinity column to sort fragments into 256 subsets on the basis of the sticky-end
Step 8: Column should sort signatures into fractions bearing the same sticky-end. These fractions must then be exposed to a laser to cleave the mass-label
Step 9: The cleaved mass labels and signature fragments can then be injected directly into an electrospray mass spectrometer for analysis. The charge of the label can be designed to be the opposite of the oligonucleotide signature. Hence if it is negative then the labels can be analysed by negative ion mass spectrometry
Key to FIG. 4
A Ion source
B Ion current
C Electrical gate
D Reflectron
E Detector
(1),(2)Preferred photocleavable linkers
Key to FIG. 8
(1)–(3)Preferred Mass Label Strutures where n≧0
(4) Mass Defect containing mass labels where n≧0 and m≧0 and X is preerably F or H
Key to FIG. 9
(1) Preferred terminal variable or Mass Series Modifying Group
(2) Preferred internal variable or mass series modifying group where n>=O and R can be arbitrary groups. For Mass Series Modifying groups R grous preferably should not ionise or fragment. Ionising groups are shown on a separate figure.

Figure 10:
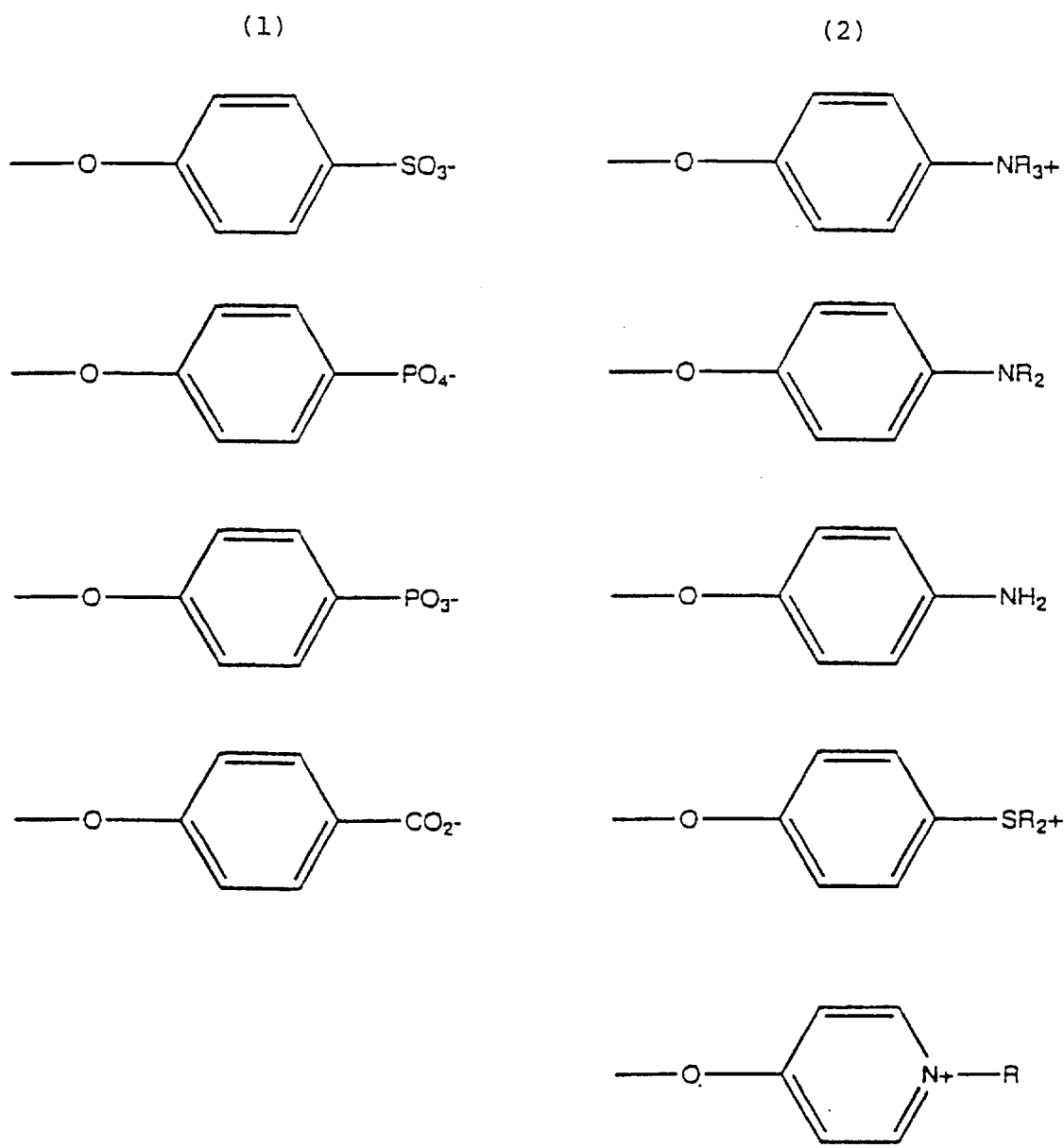
FIG. 10 shows solubilising and charge carrying groups suitable for use in the present invention.

Key to FIG. 10
(1) Negative Ion Mode Groups
(2) Positive Ion Mode Groups
Key to FIG. 11
Legend: Sample AG/1/75, 10 ng/μL, 1:1 MeOH:water, CV=45V LIVER01 1 (0.997) Sm (SG, 2×0.60), Scan ES-1.79e8 where AG/1/75 is

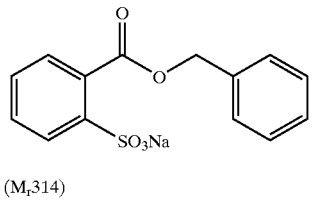

($M_r$ 314)

Key to FIG. 12
Legend: AG/1/75 5×10$^{-7}$M 20 ul/min infusion in MeOH/H$_2$O 1:1 LPOOL3 13 (0.496) Cm (9:13), Scan ES+1.89e6
Key to FIG. 13
Legend: Sample AG/1/75, 10 ng/μL, 1:1 MeOH:water, CV=1=75V LIVER02 1(0.998) Sm (SG, 2×0.60), Scan ES-4,37e7 where AG/1/75 is

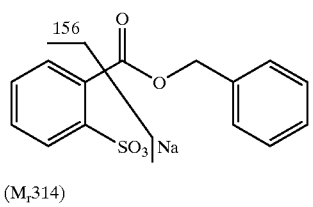

($M_r$ 314)

Key to FIG. 14
Legend: DNA 1:5D in MeOH:H2O+0.2%FORMIC 45V +/-SWITHING
(1): LPOOL5 9(0.628) Cm (2:13), 1:Scan ES-4.56e3
(2): LPOOL5 3(0.243) Cm (3:10), 2:Scan ES+1.13e5
Key to FIG. 15
Legend: DNA 1:5D in MeOH:H2O+0.2%AMMONIA 45V +/-SWITCHING
(1): LPOOL6 11 (0.761) Cm (4:12), 1:Scan ES-1.37e4
(2): LPOOL6 10 (0.726) Cm (2:11), 2:Scan ES+8.13e4
Key to FIG. 16
Legend: DNA+AG/1/75+0.2%FORMIC LOOP INJ +/-ES
(1): LPOOL9 14 (0.800) Cm (11:18), 2:Scan ES+1.04e6
(2): LPOOL9 14 (0.771) Cm (12:18), 1:Scan ES-4.20e3
Key to FIG. 17
Legend: DNA+AG/1/75+0.2%FORMIC LOOP INJ +/-ES
(1): LPOOL10 13 (0.747) Cm (11:17), 2:Scan ES+1.86e6
(2): LPOOL10 11 (0.608) Cm (11:17), 1:Scan ES-3.23e3
Key to FIG. 17
Legend: DNA+AG/1/75+0.2%FORMIC LOOP INJ +/-ES
(1): LPOOL9 14 (0.800) Cm (13:17–(22:29+4:7)) 2:Scan ES+1.02e6, (Background subtracted)
(2): LPOOL9 16 (0. 861) Cm (16:19–(23:29+9:13)) 1:Scan ES-2.70e3, (Background subtracted)
Key to FIG. 19
Legend: DNA+AG/1/75+0.2%AMMONIA LOOP INJ +/-ES
(2): LPOOL10 13 (0.747) Cm (13:14–(6:8+22:25) 2:Scan ES+2.93e6, (Backgrond subtracted)
(2): LPOOL10 11 (0.608) Cm (11:16–(8+26)), 1:Scan ES-1.03e3, (Background subtracted)

Key to FIG. 20
Legend: FT23 (only)(–ve ion) 4 pmol/ul, LPOOL2 3 (0.266) Cm (2:24), 2:Scan ES–7.35e5

Key to FIG. 21
Legend: FT23 (only)(+ve ion) 4 pmol/ul, LPOOL2 5 (0.381) Cm (2:24), 1:Scan ES+3.68e6

Key to FIG. 22
Legend: F23/OLIGO (–ve ion) 4 pmol/ul, LPOOL1 18(1.405) Cm (3:25), (Oligonucleotide mol wt≅3,000), 2:Scan ES–3.21e5

Key to FIG. 23
Legend: F23/OLIGO(+ve ion) 4 pmol/ul, LPOOL1 11 (0.830) Cm (4:26), (oligonucleotide mol wt≅3,000), 1:Scan ES+2.03e6

What is claimed is:

1. A method for determining hybridisation of an array of probes with a target nucleic acid, which method comprises:

(a) contacting target nucleic acid with each hybridisation probe of the array under conditions to hybridise the probe to the target nucleic acid, and optionally removing unhybridised material, wherein each probe comprises a mass label linked to a known base sequence of predetermined length wherein each mass label of the array is cleavable linked to its respective known base sequence;

(b) cleaving the mass label from the hybridised probe to release the mass label, wherein cleavage is induced by collision-induced-dissociation; and (c) identifying the hybridised probe by identifying the released mass label using mass spectrometry.

2. A method according to claim 1, wherein each mass label is uniquely identifiable in relation to every other mass label in the array.

3. A method according to claim 1, wherein the predetermined length of the base sequence is from 2 to 25.

4. A method according to claim 1, wherein each mass label is cleavably linked to the known base sequence by a link selected from the group consisting of a collision cleavable, a photo-cleavable, a chemically-cleavable or thermally-cleavable link.

5. A method according to claim 4, wherein the link cleaves in the ionisation chamber of the mass spectrometer.

6. A method according to claim 1, wherein each mass label is cleavably linked to its respective known base sequence by a link which is less stable to electrospray ionisation than the mass label.

7. A method according to claim 1, wherein each mass label is negatively-charged under ionisation conditions.

8. A method according to claim 1, wherein the mass label is stable to electrospray ionisation at 50V.

9. A method according to claim 1, wherein the known base sequence comprises a sticky end of an adaptor oligonucleotide containing a recognition site for a restriction endonuclease which cuts at a predetermined displacement from the recognition site.

10. A method according to claim 1, wherein the known base sequence has linked thereto a plurality of identical mass labels.

11. A method according to claim 1, wherein the mass labels and known base sequences are not separated before entry into the mass spectrometer.

12. A method according to claim 1, which is carried out in-line.

13. A method according to claim 1, wherein the target nucleic acid comprises cDNA.

14. A method for determining hybridisation of an array of probes with a target nucleic acid, which method comprises:

(a) contacting the target nucleic acid with each hybridisation probe of the array to form a sample, under conditions to hybridise the probe to the target nucleic acid, and optionally removing unhybridised material, wherein each probe comprises a mass label linked to a known base sequence or predetermined length;

(b) preparing the sample for mass spectrometry by matrix-assisted laser desorption ionisation;

(c) cleaving the mass label from the hybridised probe, wherein cleavage is induced by collision-induced-dissociation; and (d) identifying the hybridised probe by identifying the released mass label by mass spectrometry.

15. A method according to claim 14, wherein each mass label is uniquely identifiable in relation to every other mass label in the array.

16. A method according to claim 14, wherein the predetermined length of the base sequence is from 2 to 25.

17. A method according to claim 14, wherein each mass label is cleavably linked to the known base sequence by a collision cleavable link.

18. A method according to claim 14, wherein the mass label is cleaved from the hybridised probe in a mass spectrometer.

19. A method according to claim 14, wherein each mass label is negatively-charged under ionisation conditions.

20. A method according to claim 14, wherein the known base sequence comprises a sticky end of an adaptor oligonucleotide containing a recognition site for a restriction endonuclease which cuts at a predetermined displacement from the recognition site.

21. A method according to claim 14, wherein the know base sequence has linked thereto a plurality of identical mass labels.

22. A method according to claim 14, wherein the mass labels and know base sequences are not separated before entry into the mass spectrometer.

23. A method according to claim 14, which is carried out in-line.

24. A method according to claim 14, wherein the target nucleic acid comprises cDNA.

25. The method according to claim 1, wherein the mass label is cleaved from the hybridised probe by electrospray ionisation.

* * * * *

UNITED STATES PATENT AND TRADEMARK OFFICE
CERTIFICATE OF CORRECTION

PATENT NO. : 6,699,668 B1
DATED : March 2, 2004
INVENTOR(S) : Gunter Schmidt et al.

It is certified that error appears in the above-identified patent and that said Letters Patent is hereby corrected as shown below:

<u>Title page,</u>
Please add the following Items,
-- [22] PCT Filed           January 15, 1998
  [86] PCT No.:            PCT/GB98/00127
     §371 (c)(1), (2), (4) Date:    September 20, 1999
  [87] PCT Pub. No.:       WO98/31830
     PCT Pub. Date:       July 23, 1998 --

Signed and Sealed this

Twenty-third Day of November, 2004

JON W. DUDAS
*Director of the United States Patent and Trademark Office*